US009320914B2

(12) United States Patent
Toselli et al.

(10) Patent No.: US 9,320,914 B2
(45) Date of Patent: Apr. 26, 2016

(54) ENDOSCOPIC DELIVERY OF RED/NIR LIGHT TO THE SUBVENTRICULAR ZONE

(75) Inventors: Richard Toselli, Barrington, RI (US); Thomas M. Di Mauro, Southboro, MA (US); Michael Fisher, Middleboro, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 2049 days.

(21) Appl. No.: 12/041,405

(22) Filed: Mar. 3, 2008

(65) Prior Publication Data

US 2009/0222067 A1 Sep. 3, 2009

(51) Int. Cl.
*A61N 5/06* (2006.01)
*A61N 5/067* (2006.01)

(52) U.S. Cl.
CPC ......... *A61N 5/0601* (2013.01); *A61N 2005/063* (2013.01); *A61N 2005/067* (2013.01); *A61N 2005/0612* (2013.01); *A61N 2005/0659* (2013.01); *A61N 2005/0662* (2013.01)

(58) Field of Classification Search
CPC ... A61N 5/00; A61N 5/06; A61N 2005/0658; A61N 2005/0659
USPC ........................................ 607/87, 100, 88–92
See application file for complete search history.

(56) References Cited

U.S. PATENT DOCUMENTS

| | | | |
|---|---|---|---|
| 2,227,422 A | 1/1941 | Boerstler | |
| 4,105,034 A | 8/1978 | Shalaby | |
| 4,130,639 A | 12/1978 | Shalaby | |
| 4,140,678 A | 2/1979 | Shalaby | |
| 4,141,087 A | 2/1979 | Shalaby | |
| 4,205,399 A | 6/1980 | Shalaby | |
| 4,208,511 A | 6/1980 | Shalaby | |
| 5,270,300 A | 12/1993 | Hunziker | |
| 5,331,969 A | 7/1994 | Silberstein | |
| 5,445,608 A * | 8/1995 | Chen et al. | 604/20 |
| 5,464,929 A | 11/1995 | Bezwada | |
| 5,571,152 A * | 11/1996 | Chen et al. | 607/92 |
| 5,595,751 A | 1/1997 | Bezwada | |
| 5,597,579 A | 1/1997 | Bezwada | |
| 5,607,687 A | 3/1997 | Bezwada | |
| 5,618,552 A | 4/1997 | Bezwada | |
| 5,620,698 A | 4/1997 | Bezwada | |
| 5,640,978 A | 6/1997 | Wong | |
| 5,645,850 A | 7/1997 | Bezwada | |
| 5,648,088 A | 7/1997 | Bezwada | |
| 5,683,436 A | 11/1997 | Mendes | |

(Continued)

FOREIGN PATENT DOCUMENTS

RU 2200041 1/2004
RU 2222362 1/2004

OTHER PUBLICATIONS

Freundlieb, "Dopaminergic Substantia Nigra Neurons Project Topographically Organized to the Subventricular Zone and Stimulate Precursor Cell Proliferation in Aged Primates", The Journal of Neuroscience, Feb. 22, 2006, vol. 26(8), pp. 2321-2325.

(Continued)

*Primary Examiner* — Cris L Rodriguez
*Assistant Examiner* — Hao D Mai

(57) ABSTRACT

Endoscopic delivery of Red/NIR light to the Substantia Nigra to treat Parkinson's Disease in order to raise the energy levels in the substantia nigra.

2 Claims, 31 Drawing Sheets

(56) References Cited

U.S. PATENT DOCUMENTS

| | | | |
|---|---|---|---|
| 5,693,049 A | 12/1997 | Mersch | |
| 5,698,213 A | 12/1997 | Jamiolkowski | |
| 5,700,243 A | 12/1997 | Narcisco | |
| 5,700,583 A | 12/1997 | Jamiolkowski | |
| 5,707,396 A | 1/1998 | Benabid | |
| 5,720,300 A | 2/1998 | Fagan | |
| 5,728,396 A | 3/1998 | Peery | |
| 5,766,234 A | 6/1998 | Chen | |
| 5,769,878 A | 6/1998 | Kamei | |
| 5,797,868 A | 8/1998 | Leone | |
| 5,800,478 A | 9/1998 | Chen | |
| 5,846,220 A | 12/1998 | Elsberry | |
| 5,859,150 A | 1/1999 | Jamiolkowski et al. | |
| 5,910,309 A | 6/1999 | Ullrich | |
| 5,957,960 A | 9/1999 | Chen | |
| 5,995,857 A | 11/1999 | Toomim | |
| 6,083,919 A | 7/2000 | Johnson | |
| 6,358,272 B1 | 3/2002 | Wilden | |
| 6,365,726 B1 | 4/2002 | Ballinger | |
| 6,416,531 B2 | 7/2002 | Chen | |
| 6,418,344 B1 | 7/2002 | Rezai | |
| 6,527,782 B2 | 3/2003 | Hogg | |
| 6,537,304 B1 | 3/2003 | Oron | |
| 6,551,346 B2 | 4/2003 | Crossley | |
| 6,576,000 B2 | 6/2003 | Carrison | |
| 6,607,522 B1 | 8/2003 | Hamblin | |
| 6,610,713 B2 | 8/2003 | Tracey | |
| 6,713,246 B1 | 3/2004 | Reinecke | |
| 6,736,837 B2 | 5/2004 | Fox | |
| 6,921,413 B2 | 7/2005 | Mahadevan Jansen | |
| 7,013,177 B1 | 3/2006 | Whitehurst | |
| 7,081,128 B2 | 7/2006 | Hart | |
| 7,107,996 B2 | 9/2006 | Ganz | |
| 7,288,108 B2 | 10/2007 | DiMauro | |
| 7,303,578 B2 | 12/2007 | De Taboada | |
| 7,351,253 B2 | 4/2008 | DiMauro | |
| 7,354,432 B2 | 4/2008 | Eels | |
| 7,435,252 B2 | 10/2008 | Krespi | |
| 7,493,171 B1 | 2/2009 | Whitehurst | |
| 8,167,920 B2 | 5/2012 | DiMauro | |
| 2001/0047195 A1 | 11/2001 | Crossley | |
| 2001/0051766 A1 | 12/2001 | Gazdzinski | |
| 2002/0016638 A1 | 2/2002 | Mitra | |
| 2002/0029071 A1 | 3/2002 | Whitehurst | |
| 2002/0087206 A1 | 7/2002 | Hirschberg | |
| 2002/0103429 A1 | 8/2002 | deCharms | |
| 2002/0122621 A1 | 9/2002 | Li | |
| 2002/0198577 A1 | 12/2002 | Jaillet | |
| 2003/0097122 A1 | 5/2003 | Ganz | |
| 2003/0109906 A1* | 6/2003 | Streeter | 607/88 |
| 2003/0167080 A1 | 9/2003 | Hart | |
| 2003/0216797 A1 | 11/2003 | Oron | |
| 2003/0236394 A1 | 12/2003 | Schwarz | |
| 2004/0018557 A1 | 1/2004 | Qu | |
| 2004/0030368 A1 | 2/2004 | Kemeny | |
| 2004/0049249 A1 | 3/2004 | Rubery | |
| 2004/0073278 A1* | 4/2004 | Pachys | 607/88 |
| 2004/0116985 A1 | 6/2004 | Black | |
| 2004/0127892 A1 | 7/2004 | Harris | |
| 2004/0127961 A1 | 7/2004 | Whitehurst | |
| 2004/0215293 A1 | 10/2004 | Eells | |
| 2004/0219600 A1 | 11/2004 | Williams | |
| 2005/0070977 A1* | 3/2005 | Molina | 607/88 |
| 2005/0107851 A1 | 5/2005 | Taboada | |
| 2005/0107853 A1 | 5/2005 | Krespi | |
| 2005/0175658 A1 | 8/2005 | DiMauro | |
| 2005/0228291 A1 | 10/2005 | Chance | |
| 2005/0279354 A1 | 12/2005 | Deutsch | |
| 2006/0004317 A1 | 1/2006 | Mauge | |
| 2006/0100679 A1 | 5/2006 | DiMauro | |
| 2006/0155348 A1* | 7/2006 | deCharms | 607/89 |
| 2006/0161218 A1* | 7/2006 | Danilov | 607/45 |
| 2006/0167531 A1 | 7/2006 | Gertner | |
| 2006/0276861 A1 | 12/2006 | Lin | |
| 2006/0287695 A1 | 12/2006 | DiMauro | |
| 2007/0010859 A1 | 1/2007 | DiMauro | |
| 2007/0213783 A1 | 9/2007 | Pless | |
| 2007/0239235 A1 | 10/2007 | DiMauro | |
| 2008/0125836 A1* | 5/2008 | Streeter et al. | 607/89 |
| 2008/0221646 A1 | 9/2008 | DiMauro | |
| 2008/0249458 A1 | 10/2008 | Yamasaki | |
| 2008/0255646 A1 | 10/2008 | Benabid | |
| 2008/0281305 A1 | 11/2008 | Baynham | |
| 2009/0005859 A1 | 1/2009 | Keilman | |
| 2009/0054955 A1 | 2/2009 | Kopell | |
| 2009/0157141 A1 | 6/2009 | Chia | |
| 2009/0163982 A1 | 6/2009 | De Charms | |
| 2009/0222067 A1 | 9/2009 | Toselli | |
| 2010/0198316 A1 | 8/2010 | Toselli | |
| 2011/0022130 A1 | 1/2011 | DiMauro | |
| 2011/0319878 A1 | 12/2011 | DiMauro | |

OTHER PUBLICATIONS

Adam, "A Clinical Trial of Hypertonic Saline Nalas Spray in Subjects With the Common Cold or Rhinosinusitis", Archives of Family Medicine, 1998, vol. 7, pp. 39-43, American Medical Association.

Aleksandrova, Increased level of beta-amyloid in the brain of bulbectomized mice, Biochemistry, Feb. 2004, pp. 176-180, vol. 69(2). Abstract.

Aliev, Atherosclerotic lesions and mitochondria DNA deletions in brain microvessels as a central target for the development of human AD and AD-like pathology in aged transgenic mice, Ann N Y Acad Sci., Nov. 2002, pp. 45-64, vol. 977 Abstract.

Aliev, Mitochondria and vascular lesions as a central target for the development of Alzheimers disease and Alzheimers like pathology in transgenic mice, Neurological Research, Sep. 2003, pp. 665-674, vol. 25(6). Abstract.

Allcock, "Polyphosphazenes", The Encyclopedia of Polymer Science, 1988, pp. 31-41, vol. 13, Wiley Intersciences, John Wiley & Sons.

Anders, Low power laser irradiation alters the rate of regeneration of the rat facial nerve, Lasers Surg Med., 1993, pp. 72-82, vol. 13(1) Abstract.

Anders, Phototherapy promotes regeneration and functional recovery of injured peripheral nerve, Neurological Research, Mar. 2004, pp. 233-239, vol. 26.

Angell-Petersen, "Determination of fluence rate and temperature distributions in the rat brain; implications for photodynamic therapy". J. Biomed Optics, 12(1),014003-1-9 (Jan.Feb. 2007) Abstract.

Bachis, Interleukin-10 Prevents Glutamate-Mediated Cerebellar Granule Cell Death by Blocking Caspase-3-Like Activity, J. Neuroscience, May 1, 2001, pp. 3104-3112, 21(9).

Balaban, He—Ne laser irradiation of single identified neurons, Lasers Surg Med, 1992, pp. 329-337, vol. 12(3). Abstract.

Balasingam Attenuation of Astroglial Reactivity by Interleukin-10, J. Neuroscience, May 1, 1996, pp. 2945-2955, vol. 16(9).

Bernier, "Characterization of the subventricular zone of the adult human brain: evidence for the involvement of Bcl-2", Neurosci. Res. 37 (2000) 67-78.

Bhardwaj, "Hypertonic Saline Worsens Infarct Volume After Transient Focal Ischemia in Rats Editorial Comment", Stroke, 2000, vol. 31, pp. 1694-1701, American Heart Association.

Blair, "The Anterior Thalamic Head-Direction Signal is Abolished by Bilateral but Not Unilateral Lesions of the Lateral Mammillary Nucleus", J. Neuroscience, Aug. 1, 1999, 19(15) 6673-83.

Brennan, "Interleukin 10 and Arthritis", Rheumatology, 1999, pp. 293-297, vol. 38. , British Society for Rheumatology.

Brodie, Differential Effects of Th1 and Th2 Derived Cytokines on NGF Synthesis by Mouse Astrocytes, FEBS Lett., 1996, pp. 117-120, vol. 394(2), Federation of Eurpoean Biochemical Societies.

Brown et al., Gelatin/Chondroitin 6-Sulfate Misrospheres for the Delivery of Therapeutic Proteins to the Joint, Arthritis. Rheum. Dec. 1998; pp. 2185-2195, vol. 41(12), American College of Rheumatology.

Burkoth, A Review of Photocrosslinked Polyanhydrides: in situ Forming Degradable Networks, Biomaterials, 2000, pp. 2395-2404. vol. 2, Elsevier Science Ltd.

(56) References Cited

OTHER PUBLICATIONS

Byrnes, "Light promotes regeneration and functional recovery and alters the immune response after spinal cord injury", Lasers Surgery Medicine, Mar. 2005,36(3) 171-85 Abstract.
Byrnes, "Low power laser irradiation alters gene expression of olfactory ensheathing cells in vitro", Lasers Surg Med., Aug. 2005; 37(2):161-71Abstract.
Byrnes, Light Promotes Regeneration and Functional Recovery and Alters the Immune Response After Spinal Cord Injury, Lasers in Surgery and Medicine, 2005, pp. 1-15, vol. 9999.
Chen, Effects of light beam size on fluence distribution and depth of necrosis in superficially applied photodynamic therapy of normal rat brain, Photochem Photobiol., Sep. 1992, pp. 379-384, vol. 56(3) Abstract.
Cho, Effect of low-level laser therapy on osteoarthroplasty in rabbut, In Vivo, Sep.-Oct. 2004, pp. 585-591, vol. 18(5).
Cohn and Younes, "Biodegradable PEO/PLA block copolymers", Journal of Biomaterials Research,1988, pp. 993-1009, vol. 22, John Wiley and Sons.
Cohn, Polymer Preprints, Biomaterials Research Laboratory, (ACS Division of Polymer Chemistry), 1989, p. 498, vol. 30(1),(e.g. PEO/PLA).
Cottrell, Mitochondrial enzyme-deficient hippocompal neurons and choroidal cells in AD., Neurology, Jul. 2001, pp. 260-264, vol. 57(2) Abstract.
Cottrell, The role of cytochrome c oxidase deficient hippocampal neurons in Alzheimer's disease, Neuropathol Appl Neurobiol., Oct. 2002, pp. 390-396, vol. 28(5) Abstract.
Damier, "The substantia nigra of the human brain II. Patterns of loss of dopamine-containing neurons in Parkinson's disease", Brain Aug. 1999, 122(Pt. 8; 1437-48.
Davies, Axonal loss from the olfactory tracts in Alzheimer's disease, Neurobiol Aging., Jul.-Aug. 1993, pp. 353-357, vol. 14(4) Abstract.
Del Bo, Reciprocal control of inflammatory cytokines, IL-1 and IL-6, and beta-amyloid production in cultures, Neurosci Lett., Mar. 1995, pp. 70-74, vol. 188(1) Abstract.
Dugan, Fullerene-based antioxidants and neurodegenerative disorders, Parkin. Relat. Disord., 1002, Jul, pp. 243-246 , vol. 7 (3).
Ebadi, Peroxynitrite and mitochondrial dysfunction in the pathogenesis of Parkinson's disease, Antioxidants & Redox Signaling, 2003, pp. 319-335, vol. 5(3).
Duprez, "MR Imaging Findings of Cortical Blindness Following Cerebral Angiography: Is This Entity Related to Posterior Reversible Leukoencephalopathy?", Am. J. Neuroradiology 26:195-198, Jan. 2005.
Eels, Mitochondrial signal transduction in accellerated wound and retinal healing by near-infrared light therapy, Mitochondrion, 2004, pp. 559-567, vol. 4, Elsevier B.V.
Elias, Hyperthermia from interstitial laser irradiation in normal rat brain, Lasers Surg Med., 1987, pp. 370-375, vol. 7(4) Abstract.
Farin, "Endoscopic third ventriculostomy", Clin. Neurosci. Aug; 13(7):2006 ,763-70.
Giuliani, Very low level laser therapy attenuates edema and pain in experimental models, Int J Tissue React., 2004, pp. 29-37, vol. 26(1-2) Abstract.
Gonzalez, Protection against MPP+ neurotoxicity in cerebellar granule cells by antioxidants, Cell Biology Int'l, (2004) pp. 373-380, vol. 28.
Gorbatenkova, Reactivation of superoxide dismutase by the helium—neon laser irradiation, Biofizika, Jul.-Aug. 1988, pp. 717-719, vol. 33(4) Abstract.
Gorbatenkova, The red light of the helium—neon laser reactivates superoxide dismutase, Biull Eksp Biol Med., Mar. 1989, pp. 302-305, vol. 107(3) Abstract.
Grilli, Interleukin-10 modulates neuronal threshold of vulnerability to ischaemic damage, Eur. J. Neuroscience, Jul. 2000, pp. 2265-2272, 12(7). D.
Haas, Inducible nitric oxide synthase and argininosuccinate synthetase: co-induction in brain tissue of patients with Alzheimer's dementia and following stimulation with beta-amyloid 1-42 in vitro, Neurosci Lett., Apr. 5, 2002, pp. 121-125, vol. 322(2) Abstract.
Hallam, An investigation of the effect of tacrine and physostigmine on spatial working memory deficits in the olfactory bulbectomised rat, Behav Brain Res., Aug. 31, 2004, pp. 481-486, vol. 153(2) Abstract.
Hart, Comparison of the Suppressive Effects of Interleukin-10 and Interleukin-4 on Synovial Fluid Macrophages and Blood Monocytes From Patients With Inflammatory Arthritis, Immunology, Apr. 1995, pp. 536-542, vol. 84(4).
Hebeda, Light Propagation in the Brain Depends on Nerve Fiber Orientation Experimental Study, Neurosurgery, Oct. 1994, pp. 1992-1998, vol. 35(4).
Heller, "Development of Poly(Ortho Esters)", Handbook of Biodegradable Polymers, 1997, pp. 99-118, Hardwood Academic Press.
Hozumi, Characteristics of changes in cholinergic function and impairment of learning and memory-related behavior induced by olfactory bulbectomy, Behav Brain Res., Jan. 2003,pp. 9-15, vol. 138(1) Abstract.
Huell, Interleukin-6 is present in early stages of plaque formation and is restricted to the brains of Alzheimer's disease patients, Acta Neuropathol (Berl), 1995, pp. 544-551, vol. 89(6) Abstract.
Iakymenko, Regulatroy role of low-intensity laser radiation on the status of antioxidant system, Ukr. Biokhim Zh., Jan.-Feb. 2001, pp. 16-23, vol. 73(1) Abstract.
Itoh, Defects of Cytochrome c Oxidase in the Substantia Nigra of Parkinson's Disease: An Immunohistochemical and Morphometric Study., Mov. Disord., Jan. 1997, pp. 9-16, vol. 12(1).
Ji, Interstitial photoradiation injury of normal brain, Lasers Surg Med, 1992, pp. 425-431, vol. 12(4) Abstract.
Johanson, Choroid Plexus Recovery After Transient Forebrain Ischemia: Role of the Growth Factors and Other Repair Mechanisms, Cell. Mol. Neurobiol., 2000, pp. 197-216, vol. 20(2).
Kamanli, Plasma lipid peroxidation and antioxidant levels in patients with rheumatoid arthritis, Cell Biochem Funct., Jan.-Feb. 2004, pp. 53-57, vol. 22(1) Abstract.
Kang, CD11 b+ Macrophages That Infiltrate Human Epidermis After In Vivo Ultraviolet Exposure Potently Produce IL-10 and Represent the Major Secretory Source of Epidermall L-10 Protein, J. Immunol., 1994, pp. 5256-5264, vol. 153, The American Association of Immunologists.
Karu, Suppression of Human Blood Chemiluminescence by Diode Laser Irradiation at Wavelengths 660, 820, 880 or 950 nm., Laser Ther. 1993, pp. 103-109, vol. 5.
Kelly, The Anti-inftammatory Cytokin, Interleukin (IL)-10, Blocks the Inhibitory Effect of IL-1B on Long Term Potentiation, J. Biol. Chem., 2001, pp. 45564-45572, vol. 276(49), JBC Papers in Press.
Kemnitzer and Kohn, "Degradable polymers derived from the amino acid L-Tyrosine", the Handbook of Biodegradable Polymers, 1997, pp. 251-272 Hardwood Academic Press.
Klebanov, Effect of low intensity laser light in the red range on macrophages superoxide dismutase activity, Biofizika, May-Jun. 2003, pp. 462-473, vol. 48(3) Abstract.
Kleiner-Fisman, "Subthalamic Nucleus Deep Brain Stimulation: Summary and Meta-Analysis of Outcomes", Mov. Disord., Jun. 21, 2006, Suppl. 14 S290-304.
Knoblach, Interleukin-10 Improves Outcome and Alters Proinflammatory Cytokins Expression After Experimental Traumatic Brain Injury, Exp. Neuro., 1998, pp. 143-151, vol. 153, Academic Press.
Koh, "Development of cerebrospinal fluid absorption sites in the pig and rat" Anat. Embryol (BerI), Mar. 10, 2006 (e-pub).
Koh, "Integration of the subarachnoid space and lymphatics: Is it time to embrace a new concept of cerebrospinal fluid absorption?", Cerebrospinal Fluid Research 2005, 2:6, 11 pages.
Konchugova, Immunodepressive effect of transcerebral lasers, Biull Eksp Biol Med., Apr. 1993, pp. 391-393, vol. 115(4) Abstract.
Kovacs, beta-amyloid deposition and neurofibrillary tangle formation in the olfactory bulb in ageing and Alzheimer's disease, Neuropathol Appl Neurobiol., Dec. 1999, pp. 481-491, vol. 25(6) Abstract.
Kovacs, Olfactory centres in Alzheimer's disease: olfactory bulb is involved in early Braak's stages, Neuroreport., Feb. 2001, pp. 285-288, vol. 12(2) Abstract.

(56) References Cited

OTHER PUBLICATIONS

Leung, Treatment of Experimentally Induced Transient Cerebral Ischemia With Low Energy Laser Inhibits Nitric Oxide Synthase Activity and Up-Regulates the Expression of Transforming Growth Factor-Beta 1, Lasers in Surgery and Medicine, 2002, pp. 283-288, vol. 31.
Lio, Interleukin-10 promoter polymorphism in sporadic Alzheimer's disease, Genes Immun., 2003, pp. 234-238, vol. 4.
Louin, "Selective inhibition of inducible nitric oxide synthase reduces neurological deficit but not cerebral edema following traumatic brain injury", Neuropharmacology, Feb. 2006, 50(2) 182-90, Elsevier.
Mann, Alzheimer's disease: an olfactory connection?, Mech Ageing Dev., Jan. 1099, pp. 1-15, vol. 42(1) Abstract.
Mark et al.,"Hydrogels", Concise Encyclopedia of Polymer Science and Engineering, 1990, pp. 458-459, Wiley and Sons.
Mochizuki-Oda, Effects of near-infra-red laser irradiation on adenosine triphosphate and adenosine diphosphate contents of rat brain tissue, Neuroscience Letters, 2002, pp. 207-210, vol. 323.
Nagra, "Quantification of cerebrospinal fluid transport across the cribriform plate into lymphatics of rats", Am. I. Physiol. Regul. lntegr. Compo Physiol. Jun. 22, 2006(e-pub).
Nait-Oumesmar, "Activation of the subventricular zone in multiple sclerosis: Evidence for early glial progenitors", Proc Natl. Acad Sci USA. Mar. 15, 2007 13;104(11):4694-9.
Nakao, Overexpressing Cu/Zn superoxide dismutase enhances survival of transplanted neurons in a rat model of Parkinson's disease, Nat. Med. Mar. 1995, pp. 226-231 vol. (3).
Neuman, Narrow-band red light phototherapy in perennial allergic rhinitis and nasal polyposis, Annals of Allergy, Asthma, & Immunology, Apr. 1997, pp. 399-406, vol. 78 Abstract.
Nowak, The Effect of Superpulsed Carbon Dioxide Laser Energy on Keloid and Normal Dermal Fibroblast Secretion of Growth Factors: A Serum-Free Study, Plast. Reconstr. Surg., 2000, pp. 2039-2048, vol. 105(6).
Oron, "Ga—As (808 nm) laser irradiation enhances ATP production in human neuronal cells in culture", Photomed. Laser Surg., Jun. 2007; 25(3) 180-2, Abstract.
Oron, "Low-Level Laser Therapy Applied Transcranially to Rats After Induction of Stroke Significantly Reduces Long-Term Neurological Deficits", Stroke. 2006;37:2620-2624; originally published online Aug. 31, 2006.
Ostrakhovich, Active forms of oxygen and nitrogen in blood cells of patients with rheumatoid arthritis: effect of laser therapy, Vestn Ross Akad Med Nauk. 2001, pp. 23-27, vol. 5. Abstract.
Powers, Light dosimetry in brain tissue: an in vivo model applicable to photodynamic therapy, Lasers Surg Med., 1986, pp. 318-322, vol. 6(3) Abstract.
Prehn, Protective Effect of Transforming Growth Factor-Bl on B-Amyloid Neurotoxicity in Rat Hippocampal Neurons, Mol. Pharm., Feb. 1996, pp. 319-328, vol. 49(2), The American Society for Pharmacology and Experimental Therapeutics.
Qiu, Interleukin-6, beta-amyloid peptide and NMDA interactions in rat cortical neurons, J Neuroimmunol, 2003, pp. 51-57, vol. 139(1-2) Abstract.
Ren, Transforming Growth Factors-B Protect Primary Rat Hippocampal Neuronal Cultures From Degeneration Induced by B-amyloid Peptide, Brain. Res., Sep. 2, 1996, pp. 16-24, vol. 732 (1-2), Elsevier Science BV.
Rivas, Systemic Suppression of Delayed-Type Hypersensitivity by Supernatants From UV-Irradiated Keratinocyles, J. Immun, Dec. 15, 1992, pp. 3865-3871, vol. 149(12), The American Association Immunologists.
Romm, Action of laser radiation on the peroxide chemiluminescence of wound exudate, Biull Eksp Biol Med., Oct. 1986, pp. 426-428, vol. 102(10). Abstract.
Sawada, Interleukin-10 Inhibits Both Production of Cytokines and Expressoin of Cytokine Receptors in Microglia, J. Neurochemistry, 1999, pp. 1466-1471, vol. 72, Lippincott Williams & Wilkins.
Schindl, Low-Intensity Laser Therapy: A Review, Journal of Investigative Medicine, Sep. 2000, pp. 312-326, vol. 48(5).
Schmidt, Evaluation of Photodynamic Therapy Near Functional Brain Tissue in Patients With Recurrent Brain Tumors, Journal of Neuro-oncology, 2004, pp. 201-207, vol. 67, Kluwer Academic Publishers, The Netherlands.
Schmitt, Exposure to Ultraviolet Radiation Causes Dendritic Cells/Macrophages to Secrete Immune-Suppressive IL-12p40 Homodimers, J. Immunology, 2000, pp. 3162-3167, vol. 165.
Schwarz,"Effects of hypertonic (10%) saline in patients with raised intracranial pressure after stroke" Stroke, 2002, 33, pp. 136-140, American Heart Association.
Serot, A Cytokine Cascade Including Prostaglandin E2,IL-4 and IL-10 is Responsible for UV-Induced Systemic Immune Suppression, J. Neuroimmunology, 2000, pp. 115-119, vol. 104.
Shan, "Enhanced De Novo Neurogenesis and Dopaminergic Neurogenesis in the Substantia Nigra of 1-Methyl-4-phenyl-1,2,3,6-Tetrahydropyridine-Induced Parkinson's Disease-Like Mice", Stem Cells, 2006, 24:1280-7.
Shirasawa, "Physiological roles of endogenous nitric oxide in lymphatic pump activity of rat mesentery in vivo" Am. J. Physiol. Gastrointest. Liver Physiol., 2000, pp. G551-G556, vol. 278, The American Physiological Society.
Shreedhar, A Cy10kine Cascade Including Prostaglandin E2, IL-4 and IL-10 is Responsible for UV-Induced Systemic Immune Suppression, J. Immunol., 1998, pp, 3783-3789, vol. 160, The American Association of Immunologists.
Snyder, Quantitation of Calcitonin Gene-Related Peptide mRNA and Neuronal Cell Death in Facial Motor Nuclei Following Axotomy and 633 nm Low Power Laser Treatment, Lasers in Surgery and Medicine, 2002, pp. 216-222, vol. 31.
Sohranji, Local and cortical effects of olfactory bulb lesions on trophic support and cholingeric function and their modulation by estrogen, J Neurobiol, Nov. 2000, pp. 61-74, vol. 45(2) Abstract.
Stefani, "Bilateral deep brain stimulation of the pedunculopontine and subthalamic nuclei in severe Parkinson's disease", Brain, 2007, 130(6), 1596-1607.
Strle, IL-10 Promotes Survival of Microglia Without Activating Akt, J. Neuroimmunology, Jan. 2002; pp. 9-19, vol. 122(1-2).
Strle, Interleukin-10 in the Brain, Crit. Rev. Immunology, 2001, pp. 427-449, vol. 21(5).
Stutzmann, GaN-based Heterostructures for Sensor Applications, Diamond and Related Materials, 2002, pp. 886-891, vol. 11, Elsevier Science BV.
Sutton, Amyloid-B peptide induced inflammatory reaction is mediated by the cytokines tumor necrosis factor and interleukin-1, J. Submicrosc.Cytol. Pathol., 1999, pp. 313-323, vol. 31(3), Elsevier Science B.V.
Szczepanik, I1-4, IL-10 and IL-13 Modulate AB)1-42)-Induced Cytokine and Chemokine Production in Primary Murine Microglia and a Human Monocyte Cell Line, J. Neuroimmunology, 2001, pp. 49-62, vol. 113.
Town, Reduced Th1 and Enhanced Th2 Immunity with Alzheimer's B-amyloid 1-42, J. Neuroimmunol., (2002), pp. 49-89, vol. 132, Elsevier Science BV.
Tsuboi, Tau pathology in the olfactory bulb correlates with Braak stage, Lewy body pathology and apolipoprotein epsilon4, Neuropathol Appl Neurobiol., Oct. 2003, pp. 503-510, (5) Abstract.
Unterberg,"Edema and Brain Trauma", Neuroscience, 2004, 1021-1029, vol. 129, Elsevier Ltd.
Vandorpe, "Biodegradable Polyphosphazenes for Biomedical Applications", Handbook of Biodegradable Polymers, 1997, pp. 161-182, Hardwood Academic Press.
Vann, "The Mammillary Bodies:Two Memory Systems in One?", Nature Reviews: Neuroscience, vol. 5 Jan. 2004,35-44.
Victor, "The irrelevance of mammillary body lesions in the causation of the Korsakoff amnesic state.", Int'l J. Neurol., 1987-8, 21-22, 51-7 Abstract.
Vink, "Novel therapies in development for the treatment of traumatic brain injury", Exp. Op. Invest. Drugs, Oct. 2002, pp. 1375-1386, vol. 11(1), Ashley Publications Ltd.

(56) References Cited

OTHER PUBLICATIONS

Vink, "Recent advances in the development of multifactorial therapies for the treatment of traumatic brain injury", Exp. Op. Invest. Drugs, 2004, pp. 1263-1274, vol. 13(10), Ashley Publications Ltd.

Vitreshchak, Laser Modification of the Blood in Vitro and in Vivo in Patients with Parkinson's Disease Bull. Exp. Biol. Med. May 2003 430-432, vol. 135(5).

Vladimirov, Molecular and cellular mechanisms of the low intensity laser radiation effect, Biofizika, Mar.-Apr. 2004, pp. 339-350, vol. 49(2).

Vladimirov, Photobiological Principles of Therapeutic Applications of Laser Radiation Biochemistry, 2004, pp. 81-90, vol. 69(1).

Vladimirov, Photoreactivation of Superoxide Dismutase by Intensive Red (Laser) Light, Free Radical Biology & Medicine, 1988, pp. 281-286, vol. 5.

Volotovskaia, Antioxidant action and therapeutic efficacy of laser irradiation blood in patients with ischemic heart disease, Vopr Kurortol Lech Fiz Kult, May-Jun. 2003, pp. 22-25, vol. 3 Abstract.

Von Der Weid, "Nitric oxide decreases pacemaker activity in lymphatic vessels of guinea pig messentry", Am. J. Physiol. Heart Circ. Physiol., Jun. 2001: 280(6) H2707-16, The American Physiology Society.

Walicke, Purification of a human red blood cell protein supporting the survival of cultured CNS neurons and its identification as catalase, J. Neuroscience, Apr. 1986, pp. 1114-1121, vol. 6(4).

Welter, "Effects of Hugh-Frequency Stimulation on Subthalamic Neuronal Activity in Parkinsonian Patients", Arch. Neurol. 2004: 61:89-96.

Wollman, In vitro cellular processes sprouting in cortex microexplants of adult rat brains induced by low power laser irradiation, Neurologic Research, Jul. 1998, pp. 470-472, vol. 20.

Wollman, Low power laser irradiation enhances migration and neurite sprouting of cultured rat embryonal brain cells, Neurological Research, Oct. 1996, pp. 467-470, vol. 18 Abstract.

Wong-Riley, Light-emitting diode treatment reverses the effect of TTX on cytochrome osidase in neurons, Neuroreport, Oct. 8, 2001, pp. 3033-3037, vol. 12(14) Abstract.

Wong-Riley, Photobiomodulation directly benefits primary neurons functionally inactivated by toxins: role of cytochrome c oxidase, J. Biol. Chem. Feb 11, 2005, pp. 4761-4771, 280(6), Epub Nov. 22, 2004. Abstract.

Yamamoto, Characteristics of memory dysfunction in olfactory bulbectomized rats and the effects of cholinergic drugs, Behav Brain Res, Feb. 1997, pp. 57-62, vol. 83(1-2) Abstract.

Yamamoto, Involvement of the olfactory system in learning and memory: a close correlation between the olfactory deficit and the course of Alzheimer's disease?, Yakubutsu Seishin Kodo, 1991, pp. 223-235, vol. 11(4) Abstract.

Yaroslavsky, Optical Properties of Selected Native and Coagulated human Brain Tissue In Vitro in the Visible and Near Infrared Spectral Range, Phys. Med. Biol., 2002, pp. 2059-2073, vol. 47.

Zawieja, "Inhibition of the active lymph pump in rat mesenteric lymphatics by hydrogen peroxide", Lymphology, Sep. 26, 1993, (3) pp. 135-142—abstract.

\* cited by examiner

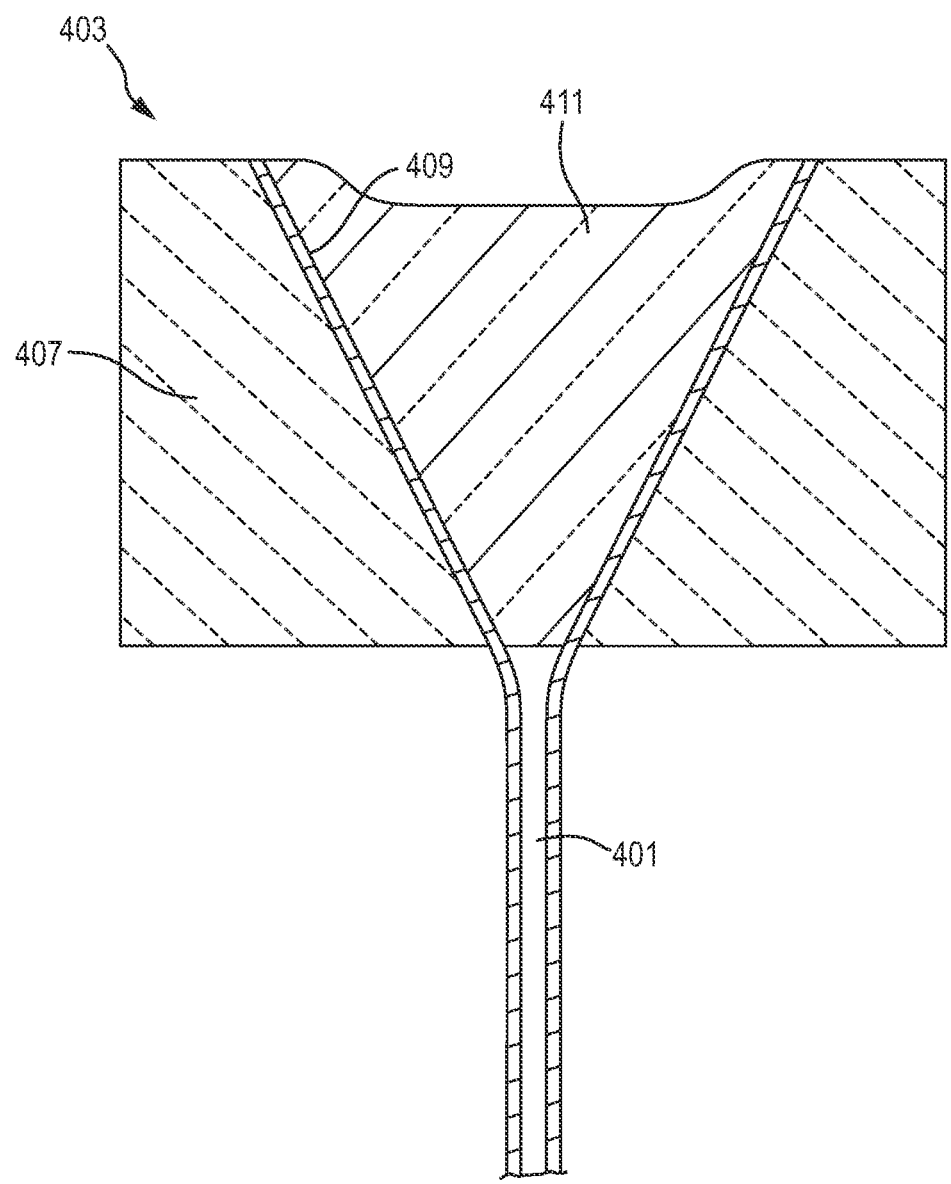

ENDOSCOPIC DELIVERY OF RED/NIR LIGHT TO THE SUBVENTRICULAR ZONE

BACKGROUND OF THE INVENTION

Decreased neuronal energy production and increased oxidative stress are believed to be major components in the onset of Parkinson's Disease. It is believed that the substantia nigra contains high levels of iron, which helps catalyze oxygen to reactive oxygen species (ROS). The ROS then degrade dopamine-containing neurons. It is further believed that neurotoxins may be the cause of decreased neuronal energy output in the substantia nigra.

The literature describes the general use of anti-oxidants as potent neuroprotective agents for Parkinson's disease. For example, Dugan, *Parkin. Relat. Disord.*, 1002, July 7, (3) 243-6, describes the use of fullerene-based antioxidants as neuroprotective drugs. In addition, oral administration of ascorbic acid has been tried as a therapy for Parkinson's Disease. To date, however, none of the therapies involving systemic administration of anti-oxidants has been shown to be successful. One possible reason for their failure was their inability to cross the blood brain barrier.

SUMMARY OF THE INVENTION

This invention relates to an implantable diode that emits red/near infrared (NIR) light onto the substantia nigra as a treatment for Parkinson's Disease (PD).

It has been reported in the literature that near red/NIR light saves neurons that have been challenged by neurotoxics from apoptosis. In particular, Wong-Riley, *J. Biol. Chem.* Feb. 11, 2005, 280(6) 4761-71, e-pub Nov. 22, 2004, reports that irradiating neurons with 670 nm red light significantly reduced neuronal cell death induced by 300 mM KCN from 83.6% to 43.5%.

The general concept of repairing brain cells through red light irradiation is also well supported by the literature. Wollman, *Neurol. Res.* July 1998, 20(5) 470-2 reports that providing daily 3.6 J/cm$^2$ doses of red light from a He—Ne laser to cortex explants resulting in caused a significant amount of sprouting of cellular processes outgrowth. Wollman concludes that the irradiation induces neurite processes sprouting and improves nerve tissue recovery. Similarly, Wollman, *Neurol. Res.* 1996 Oct. 18(5) 467-70 reports the enhanced migration and massive neurite sprouting of cultured rat embryonal brain cells subject to an 8 minute dose of a 0.3 mW, He—Ne laser. Therefore, the red light of the present invention may further cause repair and regeneration of damaged dopaminergic cells.

Therefore, in accordance with the present invention, there is provided a method of treating a patient having Parkinson's Disease, comprising the steps of:
a) irradiating a portion of a substantia nigra of the patient with an effective amount of red/NIR light.

Also in accordance with the present invention, there is provided a method of treating a patient having Parkinson's disease, comprising the steps of:
a) providing a fiber optic cable having a proximal end portion and a distal end portion;
b) implanting the fiber optic cable into the patient's brain, and
c) delivering red/NIR light through the fiber optic cable to irradiate a portion of a substantia nigra with an effective amount of red light.

Also in accordance with the present invention, there is provided a device for treating a patient having Parkinson's disease, comprising:
a) a fiber optic cable having a proximal end portion and a distal end portion;
b) an anchor attached to the proximal end portion of the fiber optic cable for fixing the fiber optic cable to the patient's skull.

Without wishing to be tied to a theory, it is believed that the therapeutic neuroprotective and neuroregenerative effects of red light described above may be due to a) an increase in ATP production in the irradiated neurons, and b) an increase in the activity of local anti-oxidant enzymes superoxide dismutase (SOD) and catalase.

It is believed that irradiating neurons in the brain with red/NIR light will likely increase ATP production from those neurons. Mochizuki-Oda, *Neurosci. Lett.* 323 (2002) 208-210, examined the effect of red light on energy metabolism of the rat brain and found that irradiating neurons with 4.8 W/cm$^2$ of 830 nm red/NIR light increased ATP production in those neurons by about 19%.

Without wishing to be tied to a theory, it is further believed that the irradiation-induced increase in ATP production in neuronal cell may be due to an upregulation of cytochrome oxidase activity in those cells. Cytochrome oxidase (also known as complex IV) is a major photoacceptor in the human brain. According to Wong-Riley, *Neuroreport*, 12:3033-3037, 2001, in vivo, light close to and in the near-infrared range is primarily absorbed by only two compounds in the mammalian brain, cytochrome oxidase and hemoglobin. Cytochrome oxidase is an important energy-generating enzyme critical for the proper functioning of neurons. The level of energy metabolism in neurons is closely coupled to their functional ability, and cytochrome oxidase has proven to be a sensitive and reliable marker of neuronal activity. Nonetheless, there is some doubt of an association between defects in cytochrome c oxidase in the substantia nigra and Parkinson's Disease. Itoh, *Mov. Disord.* January 1997, 12(1) 9-16.

By increasing the energetic activity of cytochrome oxidase, the energy level associated with neuronal metabolism may be beneficially increased. Indeed, the literature reports that red light reverses the inhibitory effects of neurotoxins upon cytochroame oxidase activity, leading to increased energy metabolism in neurons functionally inactivated by toxins. Wong-Riley *Neuroreport* 12(14) 2001:3033-3037 and Wong-Riley, *J. Biol. Chem.*, e-pub, Nov. 22, 2004.

According to Kamanli, *Cell Biochem. Func.* 2004, 22:53-57, catalase detoxifies hydrogen peroxide and converts lipid hydroperoxides into non-toxic alcohols, and is essential for the inhibition of inflammation related to the function of neutrophils.

Gonzalez, *Cell Biology Int'l*, 28(2004) 373-80, reports the effectiveness of catalase in enhancing the viability of PD cells in culture. In particular, Gonzalez reports that 50 U/ml catalase increased the in vitro viability of cerebellar granule cells exposed to MPP+ neurotoxin from about 50% to about 75%. Furthermore, it is believed that catalase is superior to the anti-oxidants recited in the prior art because it is not only an anti-oxidant, it is also neurotrophic towards CNS neurons. See Wallicke, *J. Neuroscience*, April 1986, 6(4), 1114-21.

Romm, *Biull. Eksp. Biol. Med.* 1986 October 102(10) 426-8 reports that laser irradiation of wounds results in a decreased chemiluminescence that is attributable to activation of catalase in the tissue fluid.

Therefore, it is believed that irradiating the substantia nigra with an effective amount of red/NIR light will therapeutically increase of the activity of catalase in the irradiated region, thereby attenuating the deleterious effect of hydrogen peroxide upon the dopamine neurons in the substantia nigra.

According to Kamanli, supra, SOD catalyses dismutation of the superoxide anion into hydrogen peroxide.

SOD has been shown to be neuroprotective in a rat model of Parkinson's disease. Nakao *Nat. Med.* Mar. 1, 1995, (3) 226-231, reports that the survival of grafted dopaminergic neurons in transgenic rats designed to overexpress Cu/Zn SOD was about four times higher than those in control rats, and there was also a similar increase in functional recovery.

Vitreshchak, *Bull. Exp. Biol. Med.* 135(5) May 2003 430-432, reports that He—Ne irradiation of blood from Parkinson's patients produced a normalization of their Cu—Zn SOD activity. This means that patients having lower than normal levels of SOD increased their SOD to near normal levels. This paper further reports a decrease in the severity of PD (from 72 to 58 points) in these patients.

The literature repeatedly reports that red/NIR light irradiation of inactivated SOD increases its activity. For example, Vladimirov, Biochemistry (Moscow) 69(1) 2004, 81-90 provides a review including the photoreactivation of Cu—Zn SOD under He—Ne laser. Karu, *Laser Ther.* 1993, 5, 103-9 reports that reactive oxygen species in human blood were found to be suppressed after laser diode illumination at 660 nm, 820 nm, 880 nm and 950 nm. This affect has been attributed by other authors to the activation of SOD or catalase. Volotovskaia *Vopr Kurortol Zizioter Lech Fiz Kult* May-June 2003(3)22-5 reports that 632 nm He—Ne laser irradiation of blood has an anti-oxidant effect as shown by activation of SOD. Ostrakhovich Vestn Ross Akad Med Nauk. 2001(5) 23-7 reports that infrared pulse laser therapy of RA patients caused an increase in SOD activity. Gorbatenkova *Biofizika,* 1988 July-August 33(4) 717-9 reports that SOD that was inactivated by hydrogen peroxide was reactivated by a 450-680 nm red light laser. Vladimirov, *Free Rad. Biol. Med.* 1988, 5(5-6) 281-6 reports the inactivation of SOD by its incubation in a low pH 5.9 solution and its subsequent reactivation by helium-neon laser light. Catalase was found to be reactivated as well. Cho, In Vivo, September-October 2004, 18(5) 585-91 reports on the use of low level laser therapy (LLLT) to treat knee joints that have been induced with OA by injection of hydrogen peroxide. SOD was reported to increase about 40% in the OA group as compared to controls.

Therefore, it is believed that irradiating the substantia nigra with an effective amount of red light will therapeutically increase of the activity of SOD in the irradiated region, thereby attenuating the deleterious effect of superoxide anion upon the dopamine neurons in the substantia nigra.

Since red/NIR light is known to induce molecular vibrations (the basis of infrared spectroscopy), one could easily theorize that the use of IR light, particularly higher energy IR (e.g. shorter wavelengths 600-900 nm) could induce vibrations in the enzymes (proteins) of interest (such as catalase or SOD). It may be that the activity of these enzymes is inhibited or inactivated by weak intermolecular attractions, such as hydrogen bonding, Van der Waals, or ion chelation, causing sub-optimal protein conformations, and that the introduction of red light energy causes molecular vibrations sufficient to disrupt these weak forces, thereby allowing the enzyme to return to it's active 3-D conformation upon relaxation. If such a mechanism of action was accurate, the adjunctive use of solutions to create slight changes in the local environment (pH, ionic strength, salvation) during the treatment could have profound effects upon the treatment, e.g. synergistic.

According to Leung, *Laser Surg. Med.* 31:283-288 (2002), nitric oxide enhances oxidative insult by reacting with superoxide anion to form a stronger oxidant, peroxynitrite, which leads to mitochondrial dysfunction, DNA damage and apoptosis. As a result, excess NO has been implicated as a contributing factor to dopaminergic cell loss causing Parkinson's disease. Ebadi, *Antioxidants & Redox Signaling,* 5(3), 2003, pp. 319-335.

Leung, supra, investigated the effect of low energy red laser after stroke in rats, and found that red light can both suppress NO synthase activity (and upregulate the expression of TGF-β1). In particular, Leung found that irradiating a portion of the rat's brain with a 660 nm red light (average power 8.8 mW, 2.64 J/cm$^2$) reduced NOS activity up to about 80% over that in unirradiated stroke rats, and up to about 60% over the NOS activity in normal rats. Leung concluded that the main findings of the study was that low energy laser may be protective by suppressing the activity of NOS and upregulating the expression of TGF-β1 in cerebral ischemia and reperfusion.

Without wishing to be theory, it is believed that irradiation of the substantia nigra portion of a Parkinson's brain will similarly therapeutically suppress NO synthase activity, thereby attenuating peroxynitrite activity.

DESCRIPTION OF THE FIGURES

FIG. 4C is a cross-section of a fiber optic implant of the present invention.

DETAILED DESCRIPTION OF THE INVENTION

Figure 1:
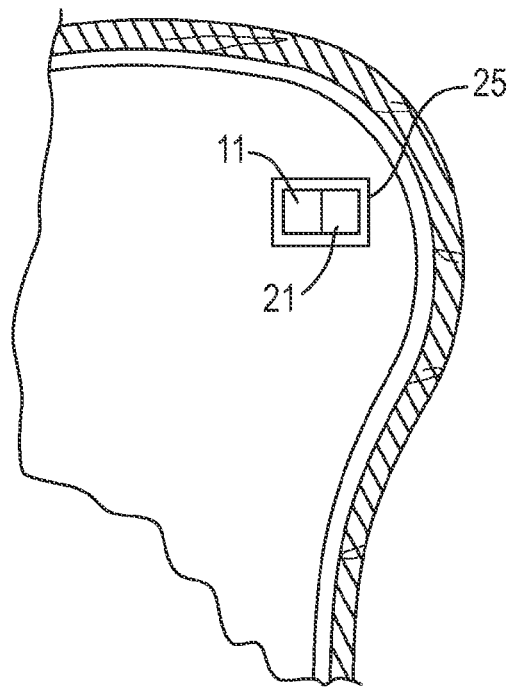
FIG. 1 is a cross-section of an LED implant of the present invention implanted within the brain of a patient having Parkinson's Disease.

Preferably, the red/NIR light of the present invention has a wavelength of between about 600 nm and about 1500 nm, more preferably between about 600 nm and about 1000 nm. In some embodiments, the wavelength of light is between 800 and 900 nm, more preferably between 825 nm and 835 nm. In this range, red light has not only a large penetration depth (thereby facilitating its transfer to the fiber optic and SN), but Wong-Riley reports that cytochrome oxidase activity is significantly increased at 830 nm, and Mochizuki-Oda reported increased ATP production via a 830 mn laser.

In some embodiments, the wavelength of light is between 600 and 700 nm. In this range, Wong-Riley reports that cytochrome oxidase activity was significantly increased at 670 nm. Wollman reports neuroregenerative effects with a 632 nm He—Ne laser.

In some embodiments, the light source is situated to irradiate adjacent tissue with between about 0.01 J/cm² and 20 J/cm² energy. Without wishing to be tied to a theory, it is believed that light transmission in this energy range will be sufficient to increase the activity of the cytochrome c oxidase around and in the target tissue. In some embodiments, the light source is situated to irradiate adjacent tissue with between about 0.05 J/cm² and 20 J/cm² energy, more preferably between about 2 J/cm² and 10 J/cm² energy.

The present inventor are aware of at least two reports of very favorable effects of red/NIR light irradiation of neuronal cells at fluences of less than 1 J/cm². As discussed above, Byrnes, Lasers Surg Med. August 2005; 37(2):161-71 found that a significant ($P<0.05$) increase in brain derived neurotrophic factor (BDNF) and glial derived neurotrophic factor (GDNF) in the 0.2 J/cm² group in comparison to the non-irradiated group. Oron, Photomed Laser Surg. June 2007; 25(3):180-2 reports that normal human neural progenitor (NHNP) cells were grown in tissue culture and were treated by Ga—As laser (808 nm, 50 mW/cm², 0.05 J/cm²). They found that the quantity of ATP in laser-treated cells 10 minutes after laser application was 7513+/−970 units, which was significantly higher ($p<0.05$) than the non-treated cells, which comprised 3808+/−539 ATP units. In sum, Oron found that the neuronal ATP level was essentially doubled by LLLT. In addition, Byrnes, *Lasers Surgery Medicine*, March 2005, 36(3) 171-85 reports that dosages as low as 0.001 stimulate cellular activity (such as DNA, RNA and protein production, proliferation and motility). Therefore, it is believed that fluences as low as about 0.01 J/cm² (and possibly even about 0.001 J/cm²) will be effective in providing therapy to the pertinent nigral neurons of the Parkinson's patient.

In some embodiments, the light source is situated to produce about 10-90 milliwatt/cm², and preferably 7-25 milliwatt/cm².

In accordance with US Patent Publication 2004-0215293 (Eells), LLLT suitable for the neuronal therapy of the present invention preferably has a wavelength between 630-1000 nm and power intensity between 25-50 mW/cm² for a time of 1-3 minutes (equivalent to an energy density of 2-10 J/cm²). Eells teaches that prior studies have suggested that biostimulation occurs at energy densities between 0.5 and 20 J/cm². Wong-Riley. *J. Biol. Chem*. Feb. 11, 2005, 280(6), 4761-71 reports that fluences as high as 30 J/cm² appear to be effective in preventing cell death in neurons exposed to the mitochondrial poison KCN. In some embodiments, the preferable energy density of the present invention is between 0.1 and about 30 J/cm², more preferably between 0.5-20 J/cm², most preferably between 2-10 J/cm². In summary, a preferred form of the present invention uses red and near infrared (red/NIR) wavelengths of 630-1000, most preferably, 670-900 nm (bandwidth of 25-35 nm) with an energy density fluence of 0.5-20 J/cm², most preferably 2-10 J/cm², to produce photobiomodulation. This is accomplished by applying a target dose of 10-90 mW/cm², preferably 25-50 mW/cm² LED-generated light for the time required to produce that energy density.

It is further believed that red/NIR light irradiation of neurons will produce a significant upregulation in brain derived neurotrophic factor (BDNF) and glial derived neurotrophic factor (GDNF). Byrnes, Lasers Surg Med. August 2005; 37(2):161-71 reports that olfactory ensheathing OECs were purified from adult rat olfactory bulbs and exposed to 810 nm light (150 mW; 0, 0.2, or 68 J/cm²). Byrnes found that a significant ($P<0.05$) increase in BDNF, GDNF and collagen expression in the 0.2 J/cm² group in comparison to the non-irradiated and high dose groups.

Of note, it has been reported that the neuroprotective effects of red/NIR light can be effected by a single irradiation on the order of minutes. Wong-Riley, *J. Biol. Chem*. 2004, e-pub November 22, reports that irradiating neurons with 670 nm red light for only ten minutes results in neuroprotection. Similarly, Wong-Riley *Neuroreport* 12(14) 2001:3033-3037 reports that a mere 80 second dose of red light irradiation of neuron provided sustained levels of cytochrome oxidase activity in those neurons over a 24 hour period. Wong-Riley hypothesizes that this phenomenon occurs because "a cascade of events must have been initiated by the high initial absorption of light by the enzyme".

Therefore, in some embodiments of the present invention, the therapeutic dose of red light is provided on approximately a daily basis, preferably no more than 3 times a day, more preferably no more than twice a day, more preferably once a day.

In some embodiments, the red light irradiation is delivered in a continuous manner. In others, the red light irradiation is pulsed in order to reduce the heat associated with the irradiation. Without wishing to be tied to a theory, it is believed that pulsed light may be more effective in achieving the vibratory oscillation of the catalase and SOD molecules.

In some embodiments, red light is combined with polychrome visible or white light Thus, there may be a substantial benefit to providing a local radiation of the substantia nigra with red laser light. The red light can be administered in a number of ways:

1) By implanting near the skull an implant having a red light LED, an antenna and a thin fiber optic terminating at the substantia nigra, and telemetrically powering the LED via an external antenna to deliver red light through the fiber optic to the substantia nigra.
2) By placing a fiber optic having a proximal light collector at the interior rim of the skull and running it to the substantia nigra, and then irradiating the proximal end via an external red light source. Red light can penetrate tissue up to about one cm, so it might be able to cross the skull and be collected by the collector.
3) By implanting a red light LED in the skull, and powering the LED via an internal battery.

In each case, there is produced an effective amount of local red or infrared irradiation around the substantia nigra. This light would then increase local ATP production, and enhance SOD and catalase activity, thereby increasing the metabolism in and reducing the oxidative stress upon the substantia nigra.

Now referring to FIG. 1, there is provided an implant for treating Parkinson's disease comprising:
a) a Red/NIR Light emitting diode (LED) 11, and
b) an antenna 21 in electrical connection with the LED.

In use, the surgeon implants the device into the brain of the patient so that the device is adjacent to a portion of the substantia nigra. The Red light produced by the implant will then irradiate that portion of the substantia nigra.

In order to protect the active elements of the device from cerebrospinal fluid ("CSF"), in some embodiments, and again referring to FIG. 1, the Red light LED is encased in a casing 25. This casing both protects the LED components from the CSF, and also prevents the LED components from eliciting a violent immune reaction In some embodiments, the casing is made of a Red/NIR light transparent material. The Red/NIR light transparent material may be placed adjacent the LED component so that Red/NIR Light may be easily transmitted therethrough. In some embodiments, the transparent casing is selected from the group consisting of silica, alumina and sapphire. In some embodiments, the light transmissible material is selected from the group consisting of a ceramic and a polymer. Suitable red light-transmissible ceramics include alumina, silica, CaF, titania and single crystal-sapphire. Suitable light transmissible polymers are preferably selected from the group consisting of polypropylene and polyesters.

In some embodiments, it may be desirable to locate the light emitting portion of the implant at a location separate from the LED, and provide a light communication means between the two sites. The light communication means may include any of a fiber optic cable, a wave guide, a hollow tube, a liquid filled tube, and a light pipe.

In some embodiments, an implanted light communication means (or "optical wave guide") is used to deliver photonic energy from the light source to a location within the brain. The optical wave guide can be embodied as an optical fiber, or internally-reflective tube (or "light pipe"). At its distal end, it may have a diffusion/diffraction surface(s), an optical lens and/or a mirror system, etc. or a combination of these elements.

In some embodiments, the optical wave guide is a light pipe. In one embodiment, the light pipe is a truncated form of the Flexible Light Pipe FLP 5 Series, marketed by Bivar Inc., which is a flexible light pipe that is 12 inches long and 2 mm in diameter, and has an outer tubing of fluorinated polymer TFE.

In some embodiments, the optical wave guide is a coiled sheet or convoluted surface that guides optical energy (light) from a source to a final target (in this case, a tissue or anatomical region of the brain, the substantia nigra). The benefit of a hollow optical wave guide is the decreased amount of light energy being absorbed by the material conduit. This benefit is mitigated by optical inefficiencies due to imperfect reflectance, but light attenuation by absorption will be greatly reduced in a hollow internally reflecting optical wave guide.

Silicone might also be used as the core and/or cladding of an optical fiber as long as the materials have different optical refractive indices. Those practiced in the art will appreciate how to manufacture silicone cores with silicone cladding.

Alternatively, a traditional optical material like glass or clear acrylic can be used as the optical wave guide core with silicone cladding that also serves as a biological boundary to impart overall device biocompatibility.

In some embodiments in which an optical wave guide is used, the distal end of the optical wave guide is a diffuser. Typically, the diffuser has a) a bulk phase comprising a light transmissive material and b) a dispersed phase comprising a light reflective material.

In some embodiments in which a fiber optic is used, the distal end of the fiber optic has a diffuser attached thereto.

In some embodiments in which a light pipe is used, the distal end of the light pipe has a diffuser or fiber optic cable attached thereto.

In some embodiments in which a fiber optic is used, the distal end of the fiber optic has a diffuser attached thereto.

Figure 2:
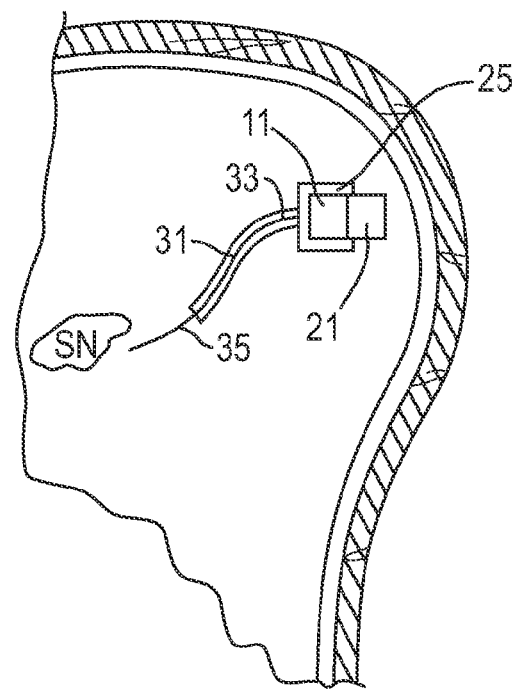
FIG. 2 is a cross-section of an implant of the present invention having a fiber optic cable and implanted within the brain of a patient having Parkinson's Disease.

Now referring to FIG. 2, there is provided an implant 1 for treating Parkinson's disease comprising:
a) a Red/NIR Light emitting diode (LED) 11,
b) an antenna 21 in electrical connection with the LED, and
c) a fiber optic cable 31 adapted to transmit Red light, the cable having a proximal end 33 connected to the LED an and a distal end portion 35.

Such a configuration would allow the distal end of the fiber optic to be located deep within the patient's brain near the substantia nigra and yet have the light source and associated components located near or in the skull in a less sensitive region. This configuration allows easier access to the light/controller should the need arise for service or maintenance, and also allow for more efficient transdermal energy transmission. Moreover, by using a hollow tube with reflective internal surfaces, light and therapeutic fluids (such as a fibroblast graft) could be delivered to the implanted device. The light source/controller implanted near the patient's skull could also be a simple, hollow chamber made to facilitate the percutaneous access described above. The advantages and benefits of this system include:

a) further removal from the deep site of the functional implant, thereby reducing risk of contamination of the deeper site by percutaneous access;
b) easier precutaneous access by being closer to the skin surface and having a larger surface area or target to access with the needle;
c) a larger volume could hold more therapeutic fluid to provide a longer duration of activity.

In use, the surgeon implants the device into the brain of the patient so that the antenna is adjacent the cranium bone and the distal end of the fiber optic cable is adjacent to the substantia nigral region of the brain.

In some embodiments, the proximal end portion of the fiber optic cable is provided with a cladding layer 41 of reflective material to insure that Red light does not escape the cable into untargeted regions of brain tissue.

Figure 3:
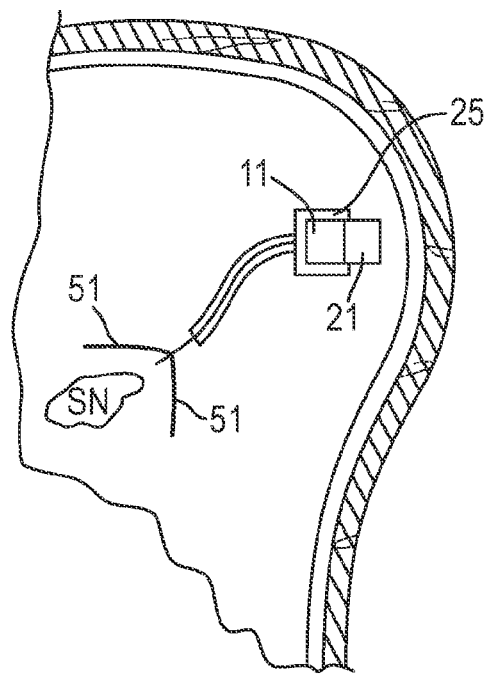
FIG. 3 is a cross-section of an implant of the present invention having a tyned fiber optic cable and implanted within the brain of a patient having Parkinson's Disease.

In some embodiments, the distal end portion of the fiber optic cable includes a plurality of fiber optic tynes 51 extending from the cable (as shown in FIG. 3). Since each of these tynes transmits Red light into brain tissue, the provision of tynes increases the volume of brain tissue that can be irradiated.

In some embodiments, the tynes located at distal end portion of the fiber optic cable are placed around the substantia nigra.

Figure 4A:
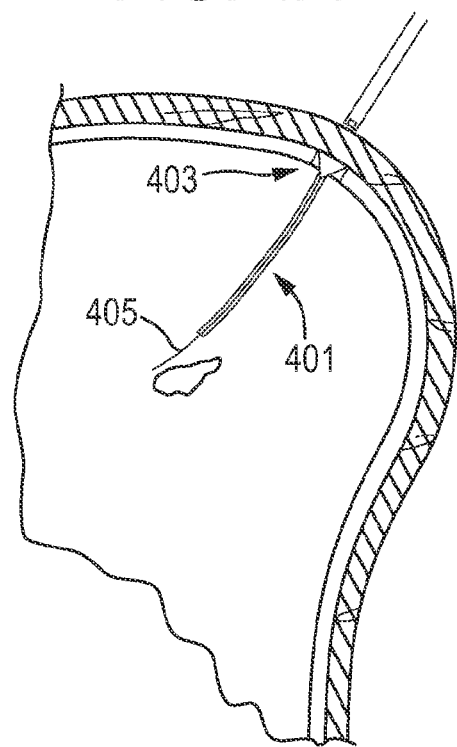
FIGS. 4A-4B are cross-sections of a fiber optic implant of the present invention implanted within the brain of a patient having Parkinson's Disease.
Figure 4B:
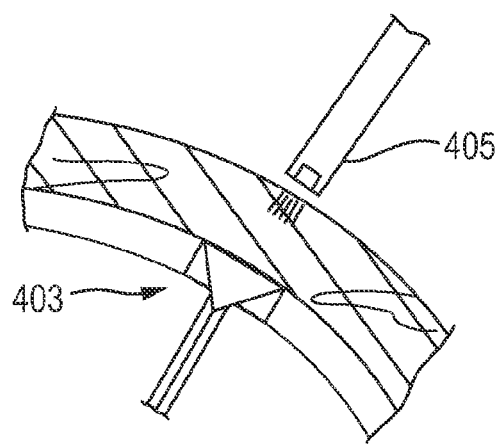

Because long wavelength red light can penetrate up to many centimeters, it might be advantageous to transcutaneously deliver the light the fiber optic. Now referring to FIGS. 4a-4c, in one embodiment, a fiber optic 401 having a proximal light collector 403 is placed at the interior rim of the skull and the distal end portion 405 of the cable (which is unclad) is run to the substantia nigra. Red light can then be delivered transcutaneously from a probe 415 to the collector 403, which will then transport the light to the substantia nigra.

In some embodiments, as in FIG. 4c, the collector 403 has a porous osteoconductive collar 407 for integrating with the bone in the skull. The collector may comprise a funnel-shaped mirror 409 (made of titanium) that connects to the fiber optic cable 401 and is filed with a red light-transparent material 411 such as silica.

To enhance the propagation of light emitted from the end of the fiber, a lens could be placed at the distal end of the fiber to spread the light, or a diffuser such as a small sheet or plate of optical material could be used to create more surface area. Alternatively, one could create a series of lateral diffusers, such as grooves or ridges, along the distal portion of end of the fiber to spread light out from 360 degrees perpendicular to the axis of the fiber, as well as emanating directly out from the end of the fiber.

Figure 5:
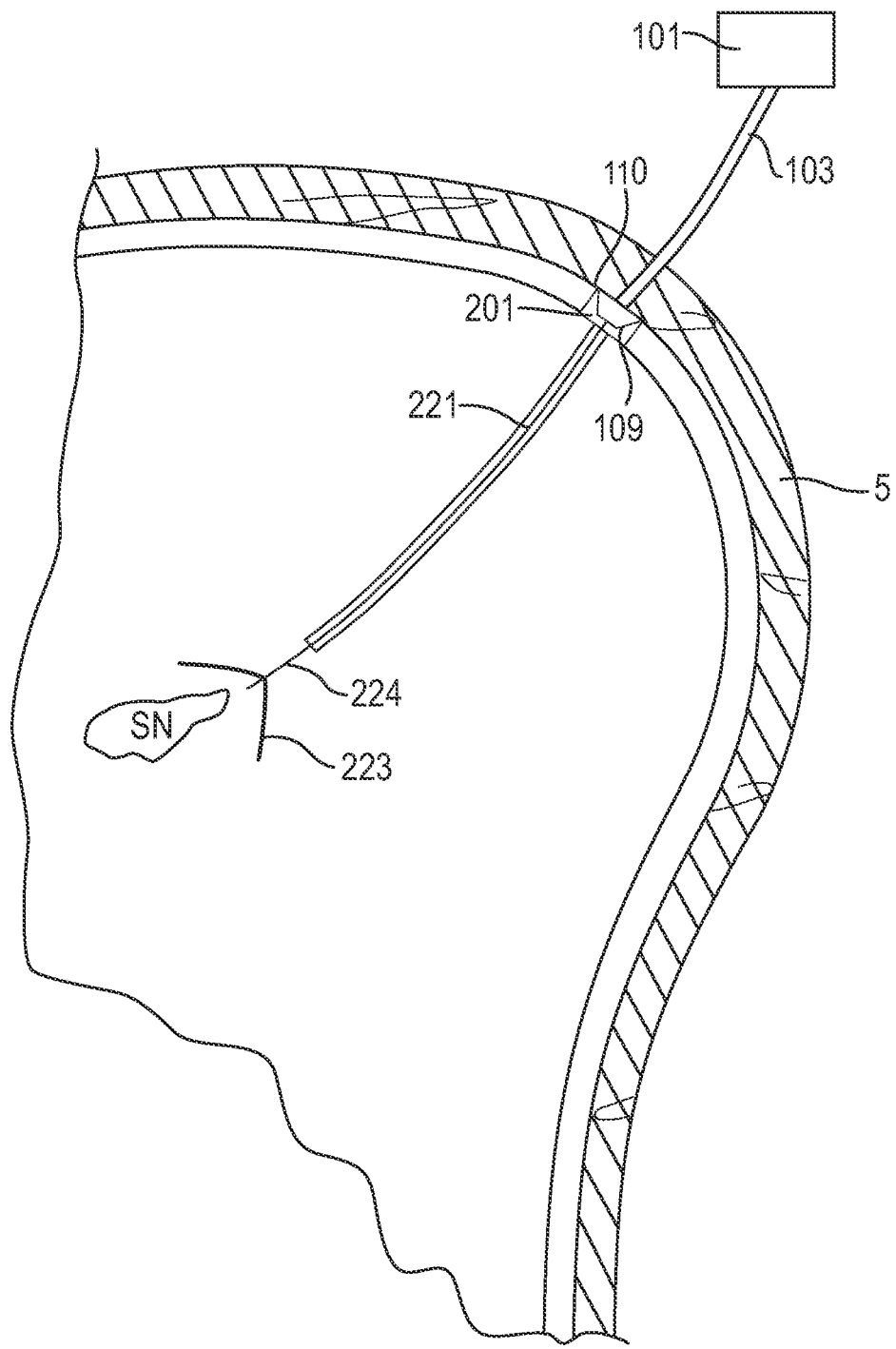
FIG. 5 is a cross-section of an implanted fiber optic implant irradiated by a light source.

Now referring to FIG. 5, there is provided an implant having an external light source. The externally based-control device has a light source 101 for generating light within the device. The light generated by this source is transmitted through fiber optic cable 103 through the patient's skin S to an internally-based light port 109 provided on the proximal surface 110 of the implant 201. The light port is adapted to be in light-communication with fiber optic cable 221 disposed upon the distal surface 203 surface of the implant. The tynes 223 disposed upon the distal portion 224 of the fiber optic cable receive the light and transmit the light to the adjacent brain tissue.

Figure 6:
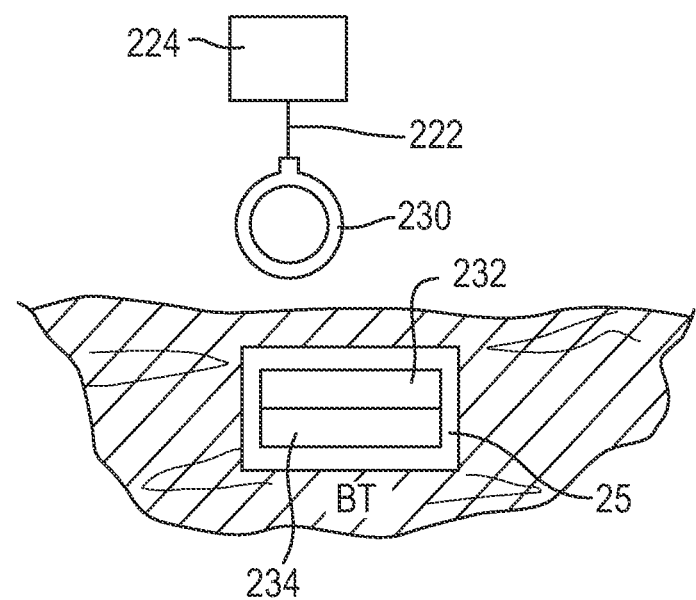
FIG. 6 is a cross-section of an Rf source energized an LED implant of the present invention.

Now referring to FIG. 6, there is provided an exemplary Red light unit having an internal light source. Externally based-control device 222 has an RF energy source 224 and an antenna 230 for transmitting signals to an internally-based antenna 232 provided on the prosthesis. These antennae 230, 232 may be electro-magnetically coupled to each other. The internal antenna 232 sends electrical power to a light emitting diode (LED) 234 disposed internally on the implant in response to the transmitted signal transmitted by the external antenna 230. The light generated by the LED travels across light transparent casing 25 and into the brain tissue BT.

Figure 7:
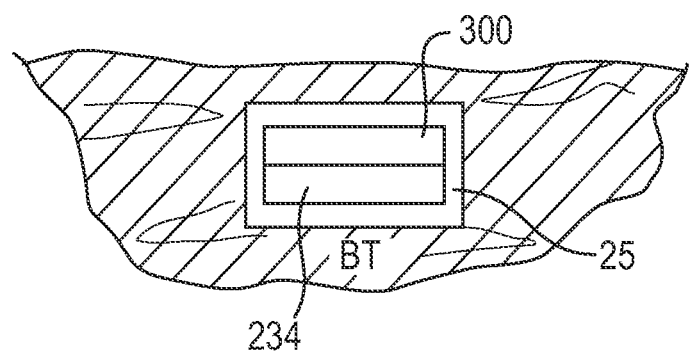
FIG. 7 is a cross-section of an LED implant of the present invention.

In some embodiments, and now referring to FIG. 7, the prosthesis having an internal light source further contains an internal power source 300, such as a battery (which could be re-chargeable), which is controlled by an internal receiver and has sufficient energy stored therein to deliver electrical power to the light source 234 in an amount sufficient to cause the desired light output.

When the implant is coupled with external energy, power can be transmitted into the internal device to re-charge the battery.

In some embodiments, the light generated by the implant is powered by wireless telemetry integrated onto or into the implant itself. In the FIG. 6 embodiment, the LED 234 may comprise a radiofrequency-to-DC converter and modulator. When radiofrequency signals are emitted by the external antenna 230 and picked up by the internal antenna 232, these signals are then converted by the receiver (not shown) into electrical current to activate the light source of the PCO unit.

In one embodiment, the implant may have an internal processor adapted to intermittently activate the LED.

In some embodiments, the telemetry portion of the device is provided by conventional, commercially-available components. For example, the externally-based power control device can be any conventional transmitter, preferably capable of transmitting at least about 40 milliwatts of energy to the internally-based antenna. Examples of such commercially available transmitters include those available from Microstrain, Inc. Burlington, Vt. Likewise, the internally-based power antenna can be any conventional antenna capable of producing at least about 40 milliwatts of energy in response to coupling with the externally-generated Rf signal. Examples of such commercially available antennae include those used in the Microstrain Strainlink™ device. Conventional transmitter-receiver telemetry is capable of transmitting up to about 500 milliwatts of energy to the internally-based antenna.

Figure 8:
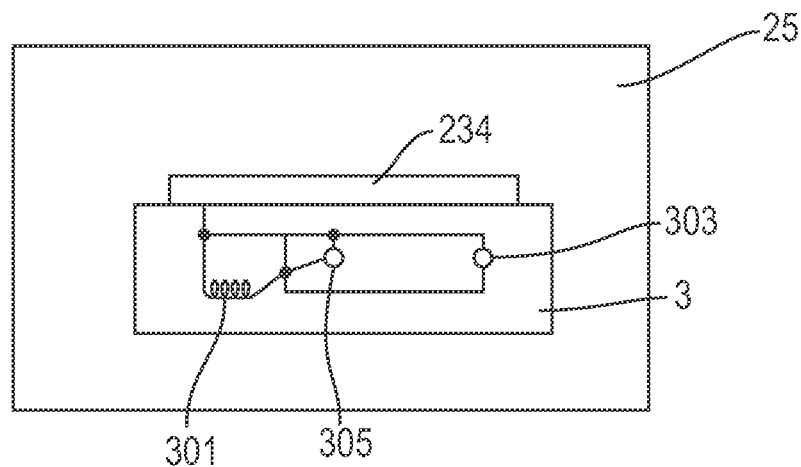
FIG. 8 is a schematic of electronics associated with an LED implant of the present invention.

In some embodiments, and now referring to FIG. 8, the implant includes a light emitting diode (LED) 234 built upon a base portion 3 of the implant, along with the required components to achieve trans-dermal activation and powering of the device. These components can include, but are not limited to, RF coils 301, control circuitry 303, a battery 305, and a capacitor. Such a device could be capable of intermittent or sustained activation without penetrating the skin, thereby avoiding trauma to the patient and/or risk of infection from skin-borne bacteria. As shown above, the accessory items needed to power and control the LED may be embedded within the implant. However, they could also be located on the surface(s) of the implant, or at a site adjacent to or near the implant, and in communication with the implant.

In some embodiments, the light source is provided on the implant and is adapted to be permanently implanted into the patient. The advantage of the internal light source is that there is no need for further transcutaneous invasion of the patient. Rather, the internally-disposed light source is activated by either a battery disposed on the implant, or by telemetry, or both. In some embodiments of the present invention using an internal light source, the light source is provided by a bioMEMs component.

Figure 9:
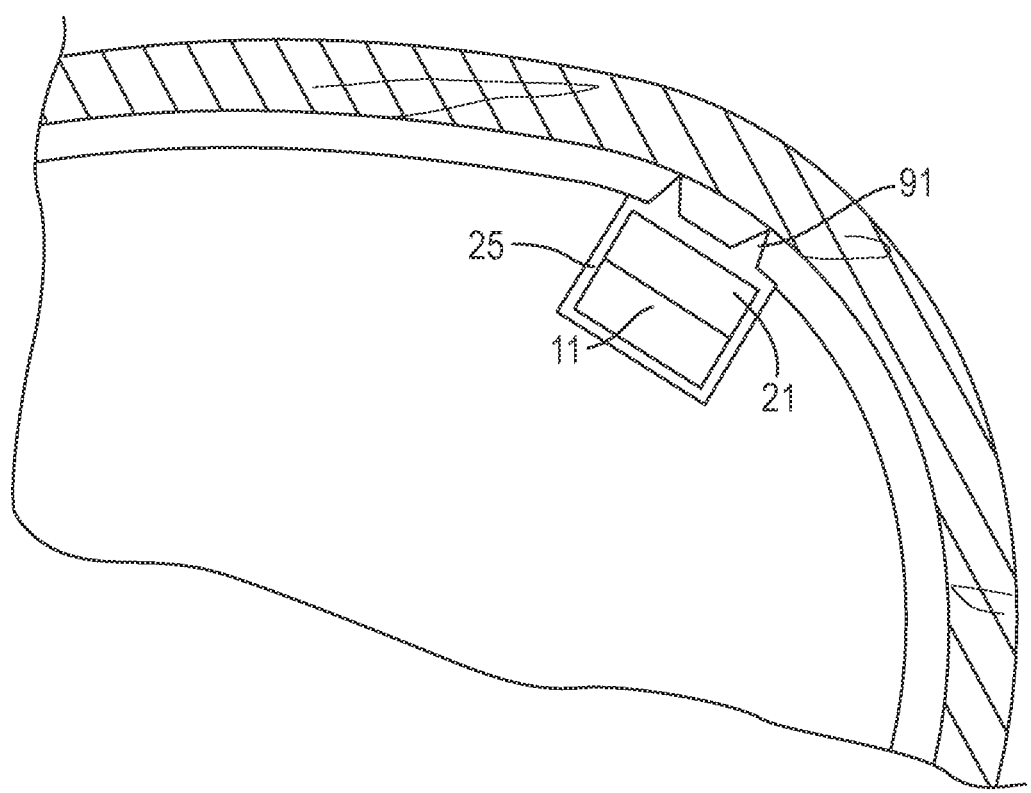
FIG. 9 is a cross-section of a toothed LED implant of the present invention implanted within the brain of a patient having Parkinson's Disease.

Because use of the present invention may require its repeated activation by Rf energy, it would be helpful if the user could be guaranteed that the implant remained in the same place within the skull. Accordingly, in some embodiments, and now referring to FIG. 9, the device of the present invention comprises anchors 91, preferably projecting from the casing 25. Preferably, the anchors are placed on the proximal side of the device, adjacent the antenna 21. In this position, the anchor may be inserted into the bone of the skull S, thereby insuring its position.

It is anticipated that the present invention would be useful in treating neurodegenerative diseases such as Parkinson's Disease, SRO Syndrome, progressive Supernuclear Palsy, parkinsonism and Alzheimer's Disease.

It is anticipated that functional benefits following red light irradiation are site-specific. In some embodiments, the fiber optic is placed to irradiate the dorsal striatum; the lateral striatum; the caudate nucleus; the putamen; the posterior putamen; the anterior putamen/caudate nucleus complex.

In some embodiments, the fiber optic is placed to irradiate the substantia nigra. Therefore, the fiber optic may be placed within about an 4 mm of the substantia nigra. The surgeon may access the substantia nigra though the brain parenchyma using stereotactic MRI guidance. As it is desirable to use a flexible material as the fiber optic in order to reduce migration, the distal end of the fiber optic may be placed near the substantia nigra with the help of a relatively stiff introducer cannula.

In some embodiments, the patient can receive a unilateral fiber optic, while in other the patient can receive bilateral fiber optic. In some embodiments, a plurality of cables is used to deliver light to each target region.

In some embodiments, a red light source or red light collector and the proximal end of the fiber optic are placed in the chest. This allows the surgeon to conduct maintenance activity on an implanted light source without having to re-open the cranium. In addition, location within the chest also lessens the chances of surface erosion.

In some embodiments, electrical stimulation of a portion of the brain (other than the substantia nigra) is carried out. In some embodiments, the stimulation is accomplished with a separate conductive wire. In others, the stimulation is in part accomplished by painting a conductive strip upon a longitudinal surface of the fiber optic cable.

Without wishing to be tied to a theory, it is believed that red/NIR light emanating from a fiber optic can safely and therapeutically irradiate a sphere of midbrain tissue having a radius of at least about 5 mm, preferably at least about 10 mm. There are at least two literature references that support this belief. First, Angell-Petersen, *J. Biomed. Optics*, 12(1), 014003-1-9 (January February 2007) studied the penetration depth of NIR light in normal and tumorous brain tissue. FIG. 4 of Angell-Petersen reported that a fiber optic inserted in brain tumor tissue will produce a fluence of 30 units at a radius of about 1 mm, a fluence of about 10 units at a radius of about 2 mm, a fluence of about 0.1 units at a radius of about 5 mm, and a fluence of about 0.01 units at a radius of about 9 mm. Angell-Petersen reports a 1000-fold decrease in intensity at 10 mm. Extrapolating from FIG. 4 of Angell-Petersen provides a fluence of about 0.001 units at a radius of about 12 mm.

Second, Oron, *Stroke*, 37, 2006, 2620-2624, reported that transcranial NIR irradiation of a rat brain with about 0.9 J/cm$^2$ of NIR light at the brain surface caused the proliferation of cells of the subventricular zone (SVZ). Because Oron discloses (in a figure) the SVZ to be located about 5 mm beneath the surface of the rat brain, it may be reasonably concluded that 0.9 J/cm$^2$ NIR light penetrated at least 5 mm in therapeutic quantities.

Therefore, using Angell-Petersen as a guide, it is believed that a fiber optic tip implanted about 1 mm adjacent the substantia nigra can produce a fluence of 30 J/cm$^2$ about 1 mm from the edge of the SN, a fluence of about 10 J/cm$^2$ at the edge of the SN, a fluence of about 0.1 J/cm$^2$ about 4 mm from the edge of the SN, a fluence of about 0.01 J/cm$^2$ about 8 mm from the edge of the SN, and a fluence of about 0.001 J/cm$^2$ about 11 mm from the edge of the SN. This latter distance corresponds to nearly 70% of the substantial length of the typical substantia nigra In some embodiments, a fiber optic is placed in the lateral ventricle and irradiates the cells of the subventricular zone (SVZ) with therapeutic amounts of red/NIR light. SVZ cells are neural progenitor cells that can facilitate neurogenesis within the substantia nigra by either migrating to the substantia nigra or by emitting neurotrophins such as GDNF and BDNF. Shan, *Stem Cells*, 2006, 24:1280-7 reports on the enhanced de novo neurogenesis in the SN in a mouse PD model, and speculates that the proliferation of neural progenitor cells is due to their migration from the SVZ. In some embodiments, the SVZ fiber optic is used by itself. In other embodiments, the SVZ fiber optic is used in conjunction with a fiber optic that irradiates the substantia nigra.

Therefore, in accordance with the present invention, there is provided a method of treating a patient having a neurodegenerative disease, comprising the steps of:
  a) providing an optical wave guide having a proximal end portion and a distal end portion;
  b) endoscopically implanting the distal end portion of the optical wave guide into a lateral ventricle, and
  c) delivering light through the optical wave guide to irradiate at least a portion of a subventricular zone with an effective amount of red/NIR light.

Although the present invention deals mainly with treating Parkinson's Disease, the present inventors are also aware that it has been reported that manipulating the stem cells of the SVZ may also be useful in treating stroke, traumatic brain injury (TBI), and multiple sclerosis. In particular, Nait-Oumesmar, *Proc Natl Acad Sci USA*. 2007 Mar. 13; 104(11): 4694-9 reports that activation of gliogenesis in the SVZ occurs in human MS and suggests the mobilization of SVZ-derived early glial progenitors to periventricular lesions, where they could give rise to oligodendrocyte precursors. Nait-Oumesmar concludes that these early glial progenitors could be a potential target for therapeutic strategies designed to promote myelin repair in MS.

Therefore, also in accordance with the present invention, there is provided a method of treating multiple sclerosis, comprising the steps of:
  a) providing a patient with multiple sclerosis having periventricular lesions, and
  b) irradiating at least a portion of a subventricular zone of the patient with an effective amount of red/NIR light.

Therefore, also in accordance with the present invention, there is provided a method of treating stroke, comprising the steps of:
  a) providing a stroke patient, and
  b) irradiating at least a portion of a subventricular zone of the patient with an effective amount of red/NIR light.

Therefore, also in accordance with the present invention, there is provided a method of treating traumatic brain injury, comprising the steps of:
  a) providing a patient having a traumatic brain injury, and
  b) irradiating at least a portion of a subventricular zone of the patient with an effective amount of red/NIR light.

Bernier, *Neurosci. Res.* 37 (2000) 67-78 at 70 reports the existence of SVZ progenitor cells in the ventral (hypothalamic) portion of the third ventricle. Accordingly, in some embodiments, red/NIR light is therapeutically shined upon the ventral (hypothalamic) portion of the third ventricle of the Parkinson's patient in order to stimulate SVZ cells.

Therefore, in accordance with the present invention, there is provided a method of treating a patient having a neurodegenerative disease, comprising the steps of:
  a) providing an optical wave guide (or LED) having a proximal end portion and a distal end portion;
  b) endoscopically implanting the distal end portion of the optical wave guide (or LED) into a third ventricle, and
  c) delivering light through the optical wave guide (or LED) to irradiate at least a portion of a subventricular zone of a hypothalamic portion of the third ventricle with an effective amount of red/NIR light.

Figure 10A:
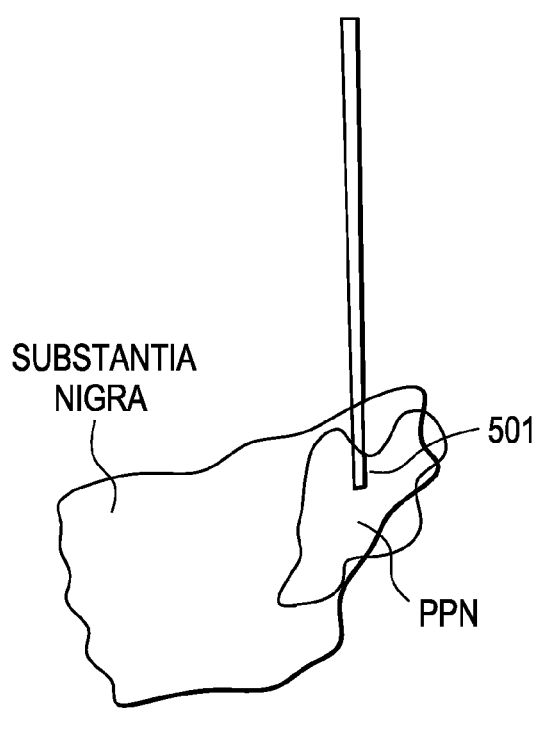
FIGS. 10*a* and 10*b* disclose an optical wave guide seated in a pedunculopontine nucleus adjacent a substantia nigra.
Figure 10B:
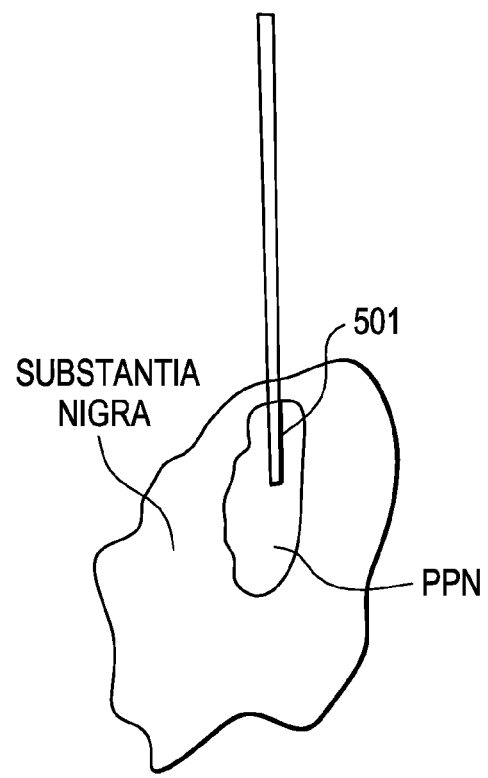

In some embodiments wherein the substantia nigra is effectively irradiated, the distal end of the fiber optic is seated in the pedunculopontine nucleus (PPN) through stereotactic guidance. The procedure for seating the fiber optic in the PPN is disclosed in Stefani, Brain, 2007, 130(6), 1596-1607 ("Stefani"). It has been noted by the present inventors that the stereotactic path to the PPN disclosed in Stefani runs essentially directly adjacent and parallel to a broad side of the substantia nigra. See color figures of FIG. 1 of Stefani and 1B in particular). If a light diffusing fiber optic is used in the place of the Stefani electrode, the distal 5 mm of such a fiber optic 501 can readily illuminate a broad portion of the substantia nigra. See FIGS. 10a and 10b herein. Thus, the seating of the fiber optic directly adjacent the SN may be safely accomplished by simply using the conventional stereotactic procedure for PPN-electrode placement to seat a fiber optic in the PPN. In this embodiment, the fluence of the light may be such that the light may provide an inhibitory dose (i.e., which, in some references, such as Ells, is over about 20 J/cm$^2$) within the PPN and a stimulating dose (between about 0.01 J/cm$^2$ and 10 J/cm$^2$) to the lateral portion of the substantia nigra. Preferably, the fiber optic is placed so that it is adjacent the middle third of the substantia nigra.

Figure 10C:
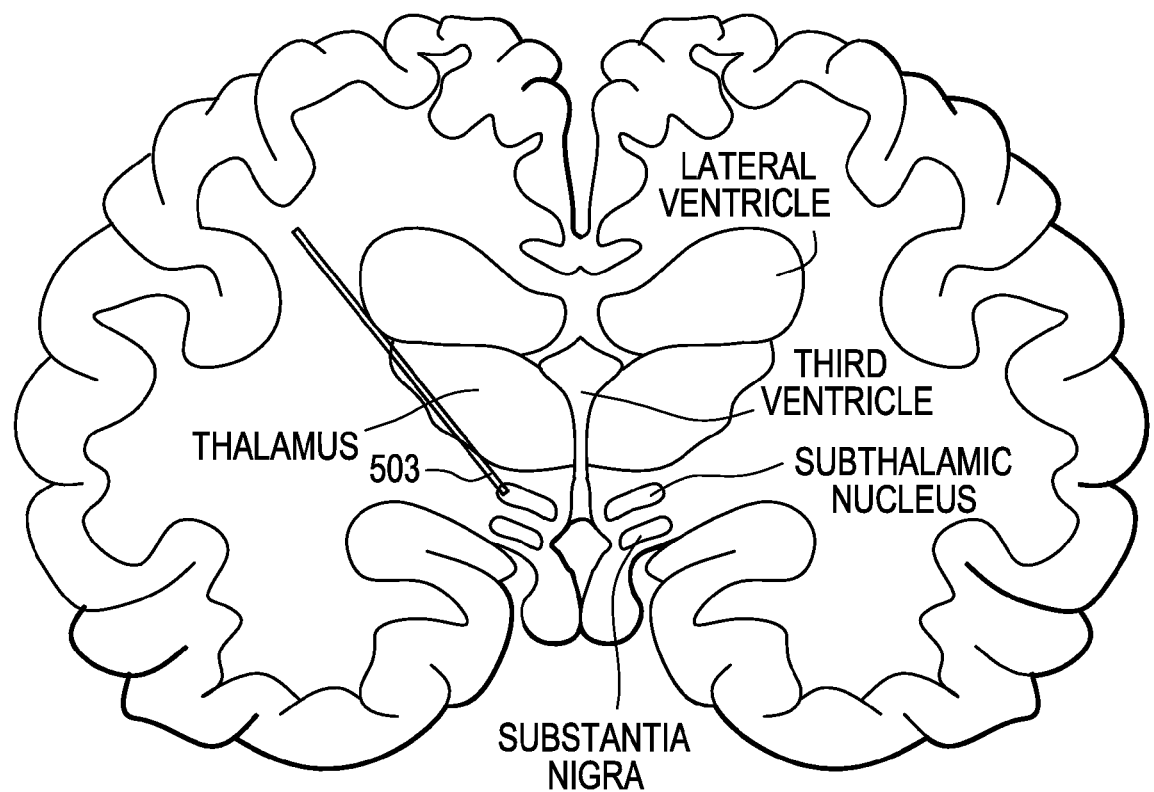
FIG. 10*c* discloses coronal cross section of a human brain in which an optical wave guide is seated in a subthalamic nucleus adjacent a substantia nigra.

In some embodiments wherein the substantia nigra is effectively irradiated, the distal end of the fiber optic is seated in the subthalamic nucleus (STN) through stereotactic guidance. The STN is located in the midbrain substantially adjacent to the upper and lateral portion of the substantia nigra. In this embodiment, the fluence of the light is such that the light may provide an inhibitory dose (i.e., over about 20 J/cm$^2$) within the STN and a stimulating dose (between about 0.01 J/cm$^2$ and 10 J/cm$^2$) to the lateral portion of the substantia nigra. Conventional stereotactic procedures for seating DBS electrodes in the STN may be used. FIG. 10c is a coronal section showing a fiber optic 503 streotactically embedded in the STN.

In some embodiments wherein the substantia nigra is effectively irradiated, the distal end of the fiber optic is seated in the substantia nigra (SN) through stereotactic guidance. In some embodiments thereof, the path used to stereotactically place an electrode in the STN is extended and used to place the distal end of the fiber optic is seated in the substantia nigra (SN). It has been noted by the present inventors that the stereotactic paths to the STN disclosed in Welter, Arch. Neurol. 2004: 61:89-96 (FIG. 1), and Stefani (FIG. 1) runs to the substantia nigra when extended distally. Thus, the seating of the fiber optic in the SN may be safely accomplished by simply using the conventional procedure for STN-electrode placement and extending the path distally. In this embodiment, the fluence of the light may be such that the light a stimulating dose (e.g., between about 0.1 J/cm$^2$ and 10 J/cm$^2$) to a portion of the substantia nigra contacting the fiber optic.

Preferably, the fiber optic is placed so that it is in the middle third of the substantia nigra. Thus, in some embodiments wherein the substantia nigra is effectively irradiated, the distal end of the fiber optic is streotactically seated in the substantia nigra (SN) by passing through the STN.

In some embodiments wherein the substantia nigra is effectively irradiated, the distal end of the fiber optic is seated within the substantia nigra.

Figure 12:
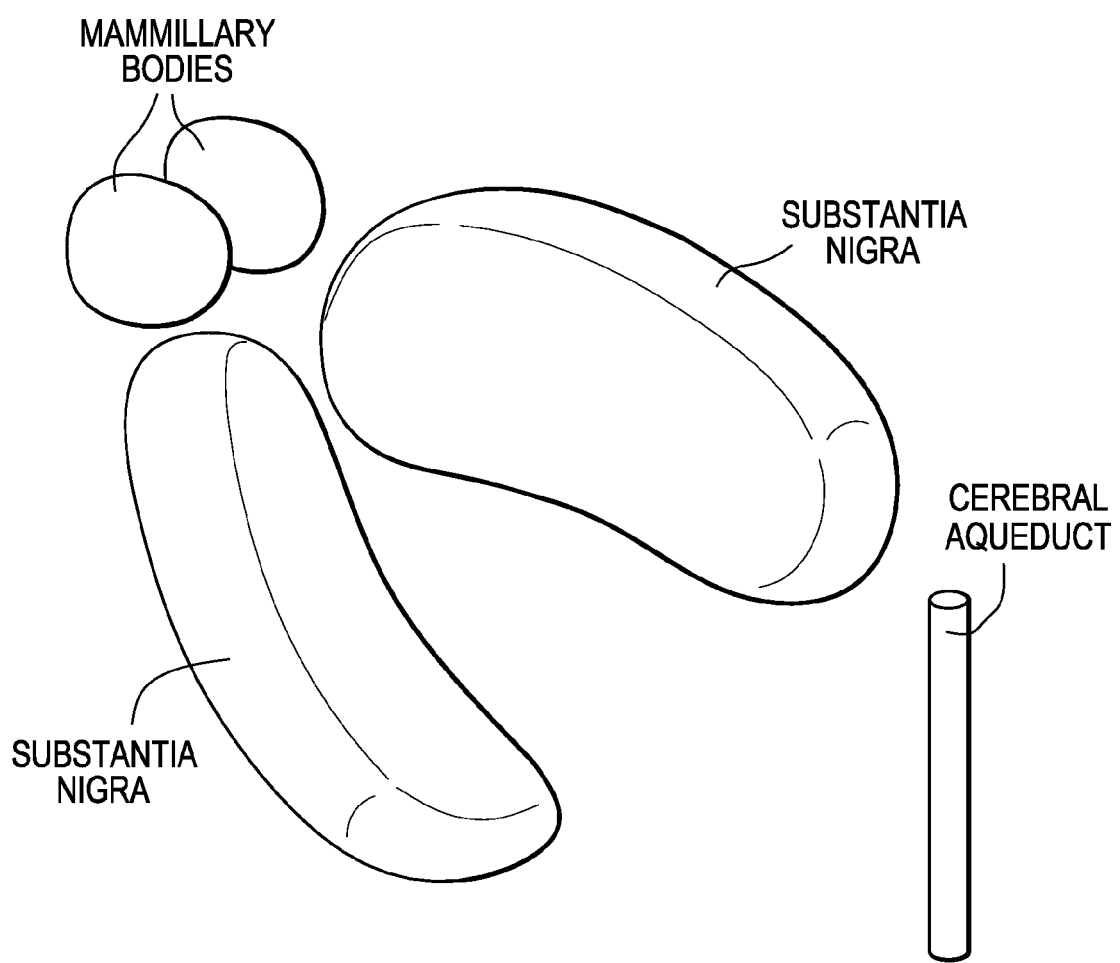
FIG. 12 discloses a perspective view of a substantia nigra and a mammillary body.
Figure 13:
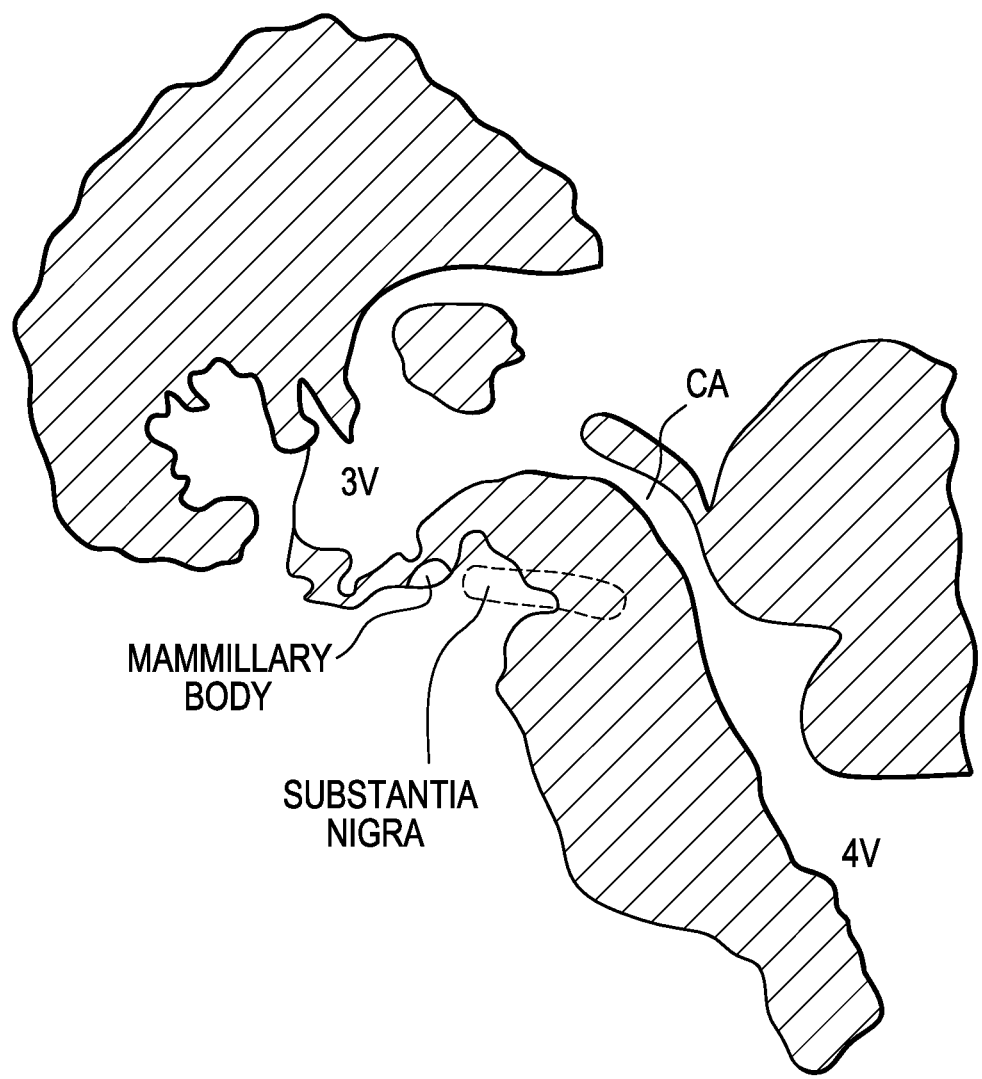
FIG. 13 discloses a saggital cross section of a human brain showing a substantia nigra and mammillary body.

As shown in FIG. 12, a horizontal section of the midbrain at the level of the mammillary bodies (MBs), the substantia nigra has a fairly central location in the midbrain. It runs substantially in the anterior-posterior direction, and its anterior tip lies adjacent to and slightly lateral to its corresponding MB. As shown in FIG. 12, a prespective view of the substantia nigra, the substantia nigra lies between the mammillary bodies and the cerebral aqueduct. Its rostral portion is substantially at the level of the MBs, and it extends caudally from that level. The depth of the posterior aspect of the substantia nigra appears to be greater than its anterior aspect. As shown in FIG. 13, a saggital centerline section of the midbrain, the anterior portion of the substantia nigra (in ghost) lies lateral to the interpeducnular fossa. Moreover, it lies at a fairly significant depth (e.g., at least 1 cm) below the floor of the third ventricle.

In some embodiments, the distal end of the fiber optic is passed through the floor of the third ventricle, through the mammillary body (MB) and into the substantia nigra. As shown in FIG. 12, the mammillary body appears to be adjacent the anterior portion of the substantia nigra. Therefore, the substantia nigra can be safely accessed by merely passing the fiber opotic through the mammillary bodies (MBs) in an anterior to posterior direction.

A review of the anatomy in and around the mammillary bodies reveals that there appears to be a great deal of redundant circuitry related to the primary functions of mamilary bodies (MBs). Vann, Nature Reviews: Neuroscience, Volume 5 January 2004, 35-44 reports that MBs primarily receive projections from the hippocampus and primarily project to the thalamus. Thus, there is an indirect route from the hippocampus to the thalamus through the MBs. However, Vann, supra, also reports the presence of tracts that project directly from the hippocampus to the thalamus. Thus, there appear to be two routes from the hippocampus to the thalamus—one direct and one indirect through the MBs. Without wishing to be tied to a theory, it is believed that the brain will respond to damage to the MBs by using the direct route from the hippocampus to the thalamus. Thus, MBs appear to have a non-critical role in memory.

The non-critical nature of mammillary bodies towards memory appears to be supported by human studies. Duprez, Am. J. Neuroradiology 26:195-198, January 2005, reports that three epilepsy patients received electrodes in their mamillary bodies without having any memory deficit. Victor, Int'l J. Neurol., 1987-8, 21-22, 51-7, concludes that mammillary bodies are irrelevant to amnesia.

Therefore, because MBs appear to have a non-critical role in memory, in some embodiments, bilateral fiber optics are passed through each of the mammillary bodies and into the adjacent substantia nigrae.

Figure 11:
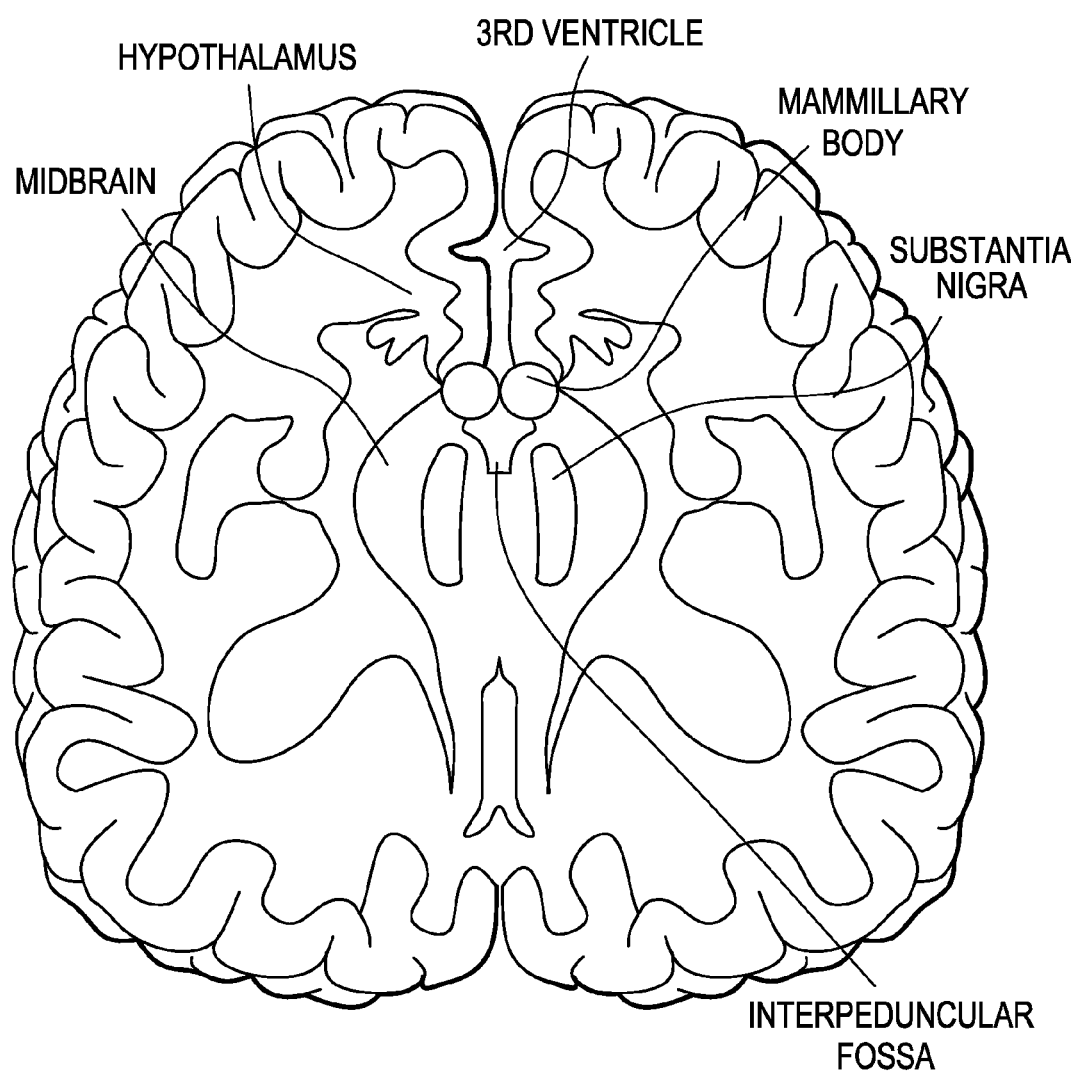
FIG. 11 discloses a horizontal cross section of an area surrounding a midbrain

In some embodiments, the MB is accessed through an anterior approach in the horizontal plane. As shown in FIG. 11, third ventricle space lies directly anterior to the mammillary bodies (as the 3$^{rd}$ ventricle floor ascends anteriorly to posteriorly in this area), while the substantia nigrae lie posterior and slightly lateral to their respective mammillary bodies.

Figure 14A:
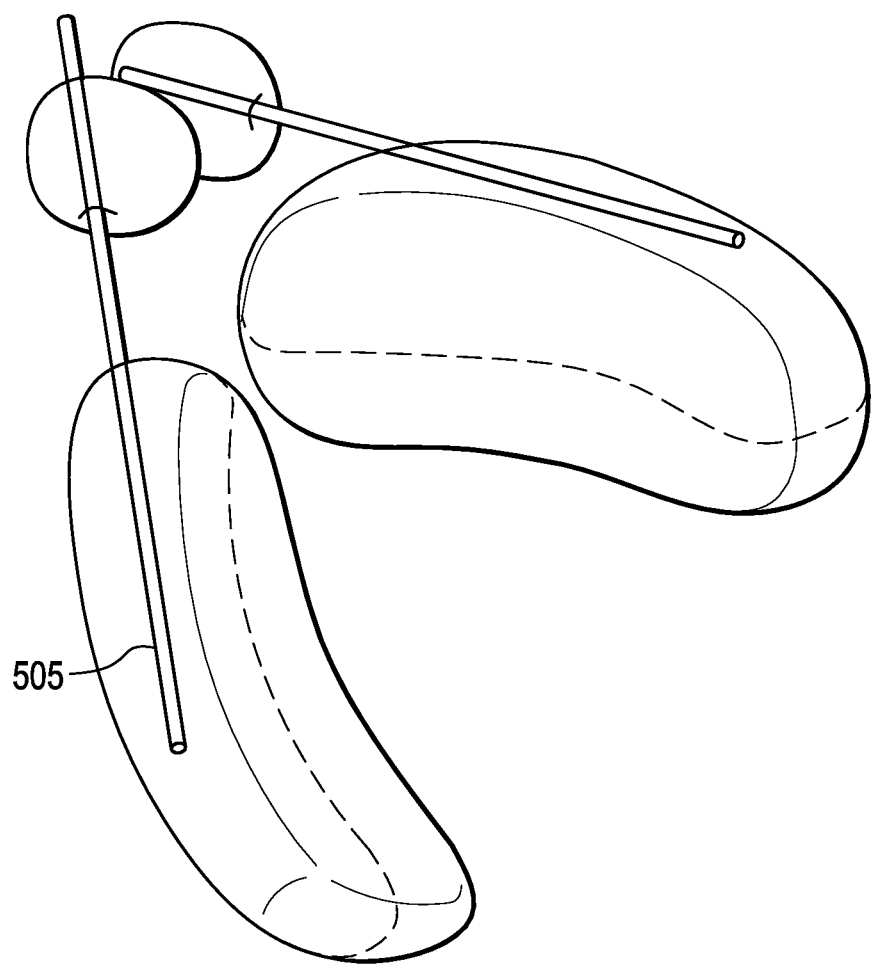
FIGS. 14*a* and 14*b* disclose a perspective and horizontal views of a straight fiber optic inserted horizontally into a substantia nigra from the third ventricle through the mammillary body.
Figure 14B:
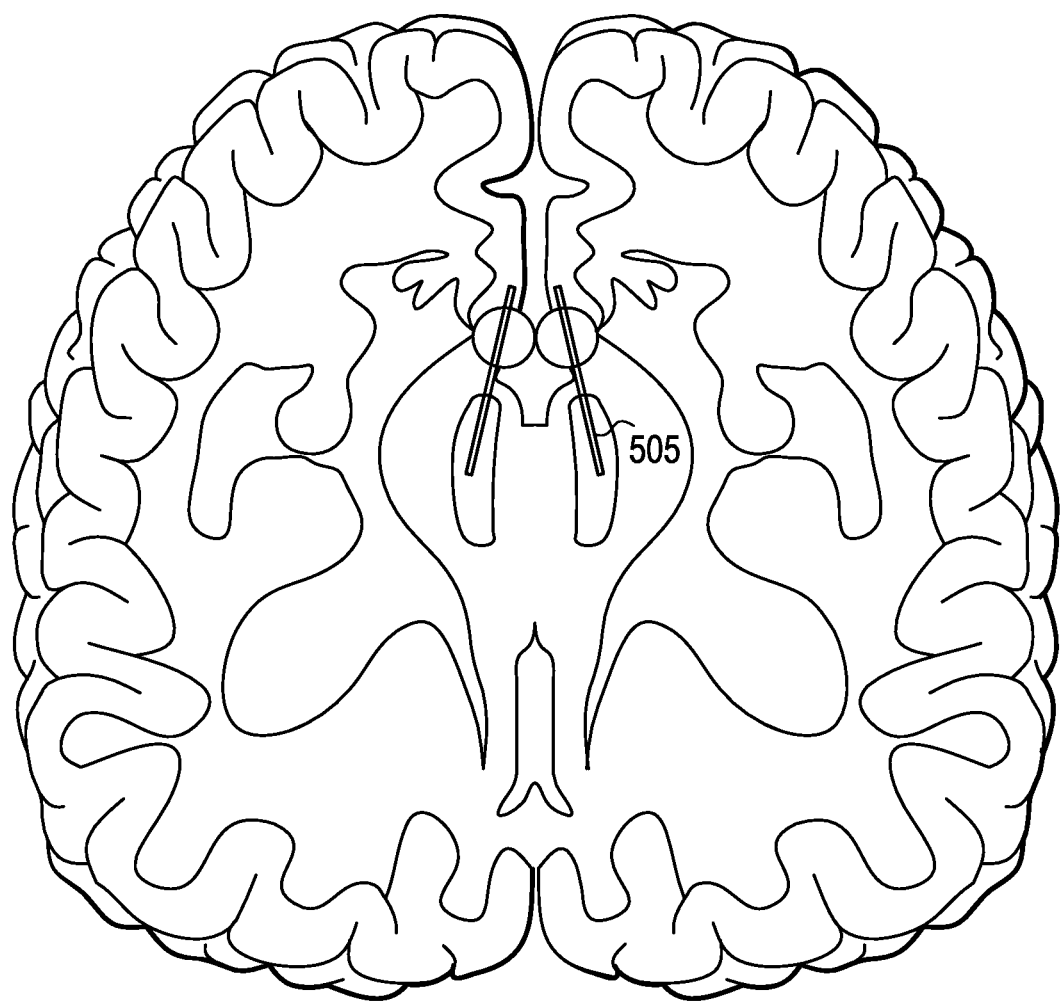

As it appears that the mammillary body lies in the same plane as its respective substantia nigra, once the fiber optic is passed through the mammillary body, it can continue to be advanced along the same line until it traverses essentially the entire substantia nigra structure. FIGS. 14a and 14b shows the midbrain with a distal end portion 505 of a fiber optic extending from the upper anterior portion of the substantia nigra to the upper posterior portion of the substantia nigra. In this embodiment, the fiber optic runs substantially along the top of the substantia nigra. Because the substantia nigra is substantially straight in the horizontal cross section, it is believed that the fiber optic can be inserted linearly through the substantia nigra and not intrude upon neighboring neural structures.

As the substantia nigra substantially descends posteriorly, the trajectory of the fiber optic passing through the mammillary body could likewise be a descending one in order to pass through as much of the substantia nigra as possible. In some embodiments, as in FIG. 15, the distal end 507 of the fiber optic is advanced through the mammillary body to contact the rostral tip of the substantia nigra adjacent the mammillary body, and is then advanced into the substantia nigra, and is advanced posteriorly to the opposite lower corner of the substantia nigra structure. In this manner, illumination of the distal end portion of the fiber optic will result in an illumination of the substantial breadth of the entire substantia nigral structure, from the upper anterior corner to the lower posterior corner.

It is noted that the fiber optic is relatively thin in relation to the substantia nigra structure. Because of this relatively thin dimension, it is believed that a thin fiber optic can suitably extend far into the substantia nigra without causing substantial damage to the overall nigral structure. For example, a typical substantia nigra has a 5 mm height, a 15 mm length and a 3 mm width, amounting to an overall volume of about 225 mm$^3$. In contrast, a fiber optic having a diameter of about 0.1 mm that traverses the length of the substantia nigra has a volume of only about 1.5 mm$^3$, or about 1% of the substantia nigra structure.

Despite the minimal invasion by the fiber optic, the fiber optic so situated is now located so as to beneficially irradiate at least half the entire substantia nigral structure with therapeutic red/NIR light. For example, if the fiber optic is emitting energy sufficient to provide 10 J/cm$^2$ of red/NIR light substantially adjacent the distal end of the fiber optic, then (assuming a penetration depth of about 2 mm) a cylinder having a radius of about 3 mm will be irradiated with between 0.1 J/cm$^2$ and 10 J/cm$^2$ of red/NIR light.

(Likewise, if the immediate vicinity is irradiated with 100 J/cm$^2$ (and so has less than optimal red/NIR light irradiation), then (assuming a penetration depth of about 2 mm) the sphere experiencing from 10-0.1 J/cm$^2$ increases to a radius of about 5 mm.) Since the typical substantia nigra has a 5 mm height, a 15 mm length and a 3 mm width, this irradiation should beneficially irradiate substantially all of the substantia nigra.

Figure 15:
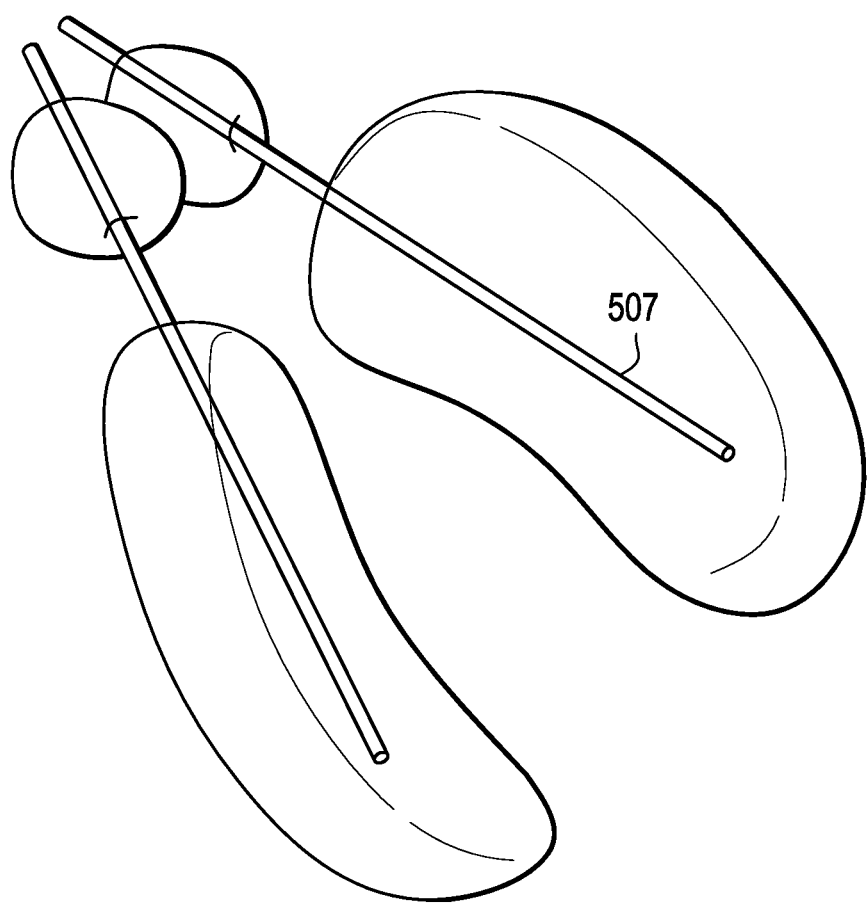
FIG. 15 discloses a perspective view of a straight fiber optic inserted diagonally downward into a substantia nigra from the third ventricle through the mammillary body.

FIG. 15 shows the midbrain-fiber optic diagram of FIG. 15, along with the expected 5 mm radiused (dotted line) zone of beneficial influence provided by red/NIR light.

Because the fiber optic will now be present in the substantia nigra, there will be essentially no dissipation of light between the fiber optic and the target structure. This will allow for the use of relatively low fluences at the tip of the fiber optic, thereby ameliorating heat and hyperirradiation concerns.

Figure 16A:
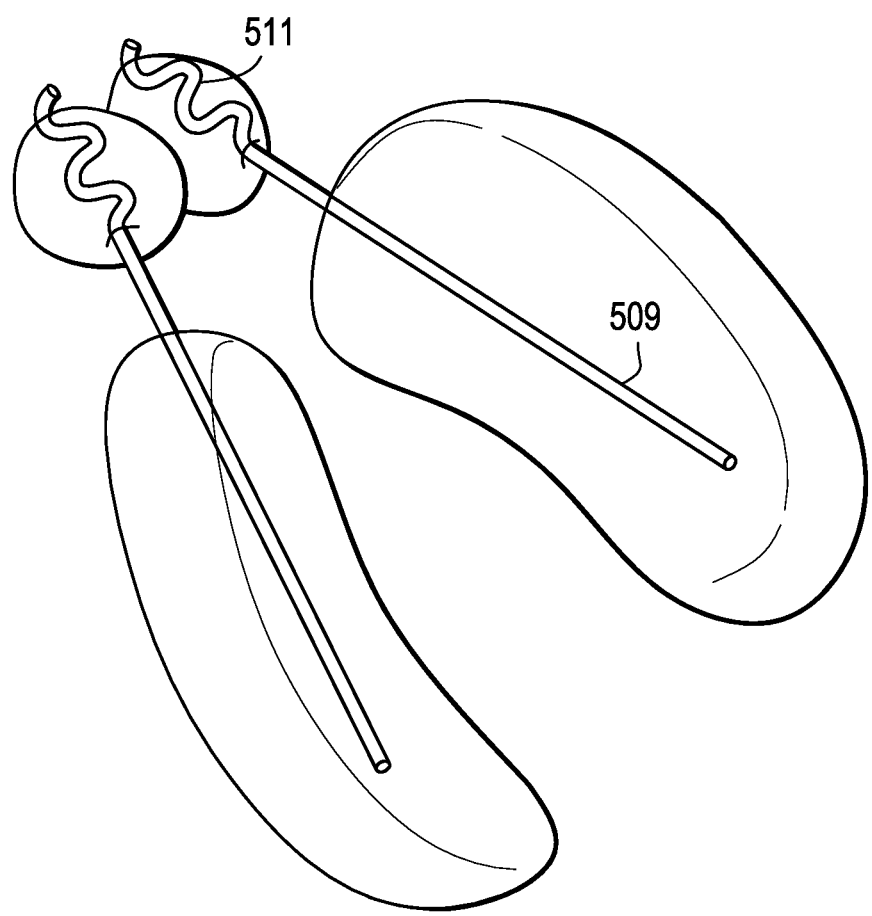
FIGS. 16a and 16b disclose a perspective and horizontal views of a fiber optic having a straight distal portion and a helical proximal portion inserted diagonally downward into a substantia nigra from the third ventricle through the mammillary body.
Figure 16B:
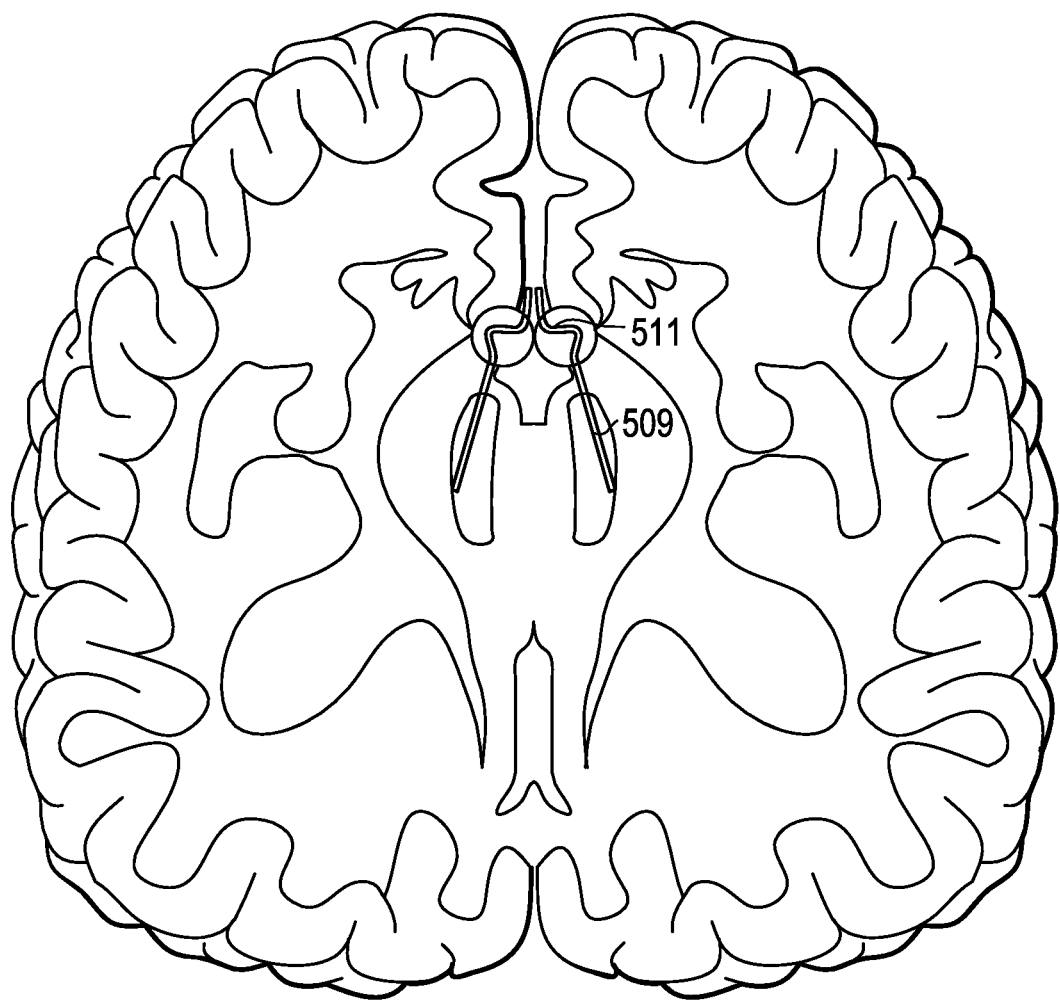

Now referring to FIG. 16a, in some embodiments associated with the traversal of the substantia nigra, the distal end portion of fiber optic has a straight distal portion and helical proximal portion. The distal end portion 509 is straight in order to minimize the invasion of the substantia nigra. The proximal portion 511 is helical in order to provide a sound anchor within the mammillary body. FIG. 16b shows a distally straight-proximally helical fiber optic embedded within the midbrain.

Figure 17A:
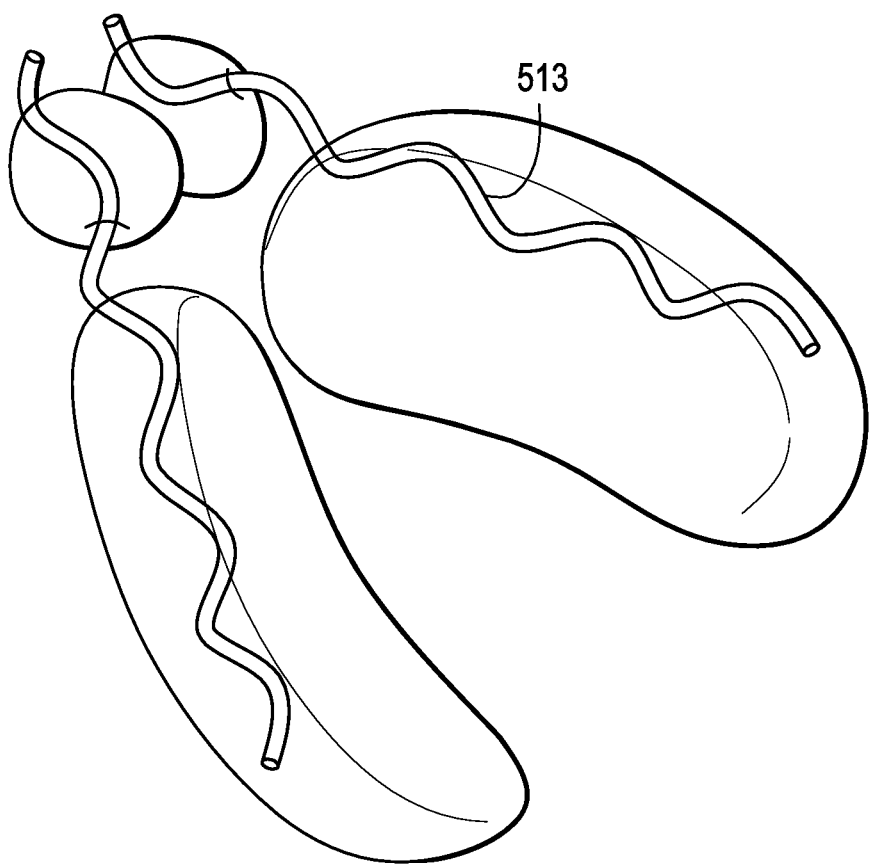
FIGS. 17a and 17b disclose a perspective and horizontal views of a helical fiber optic inserted horizontally into a substantia nigra from the third ventricle through the mammillary body.
Figure 17B:
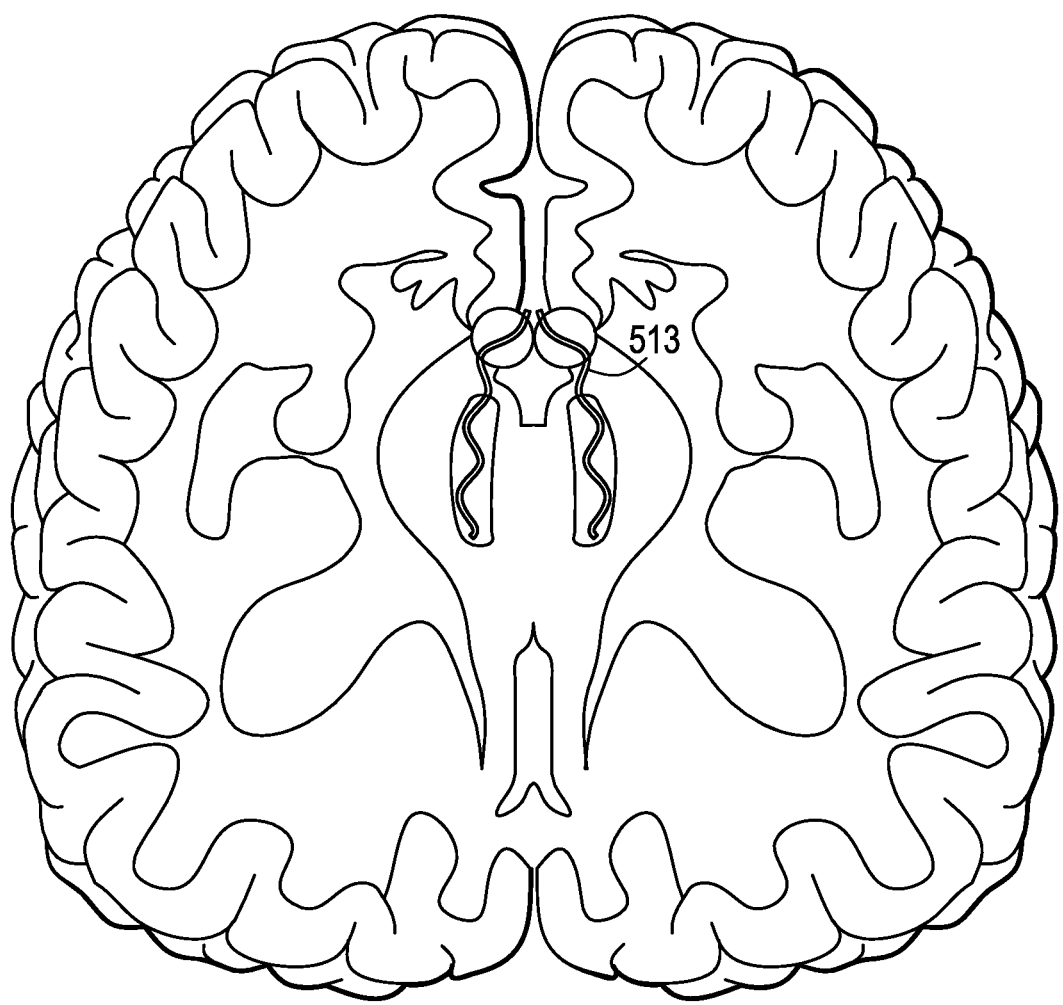
Figure 18:
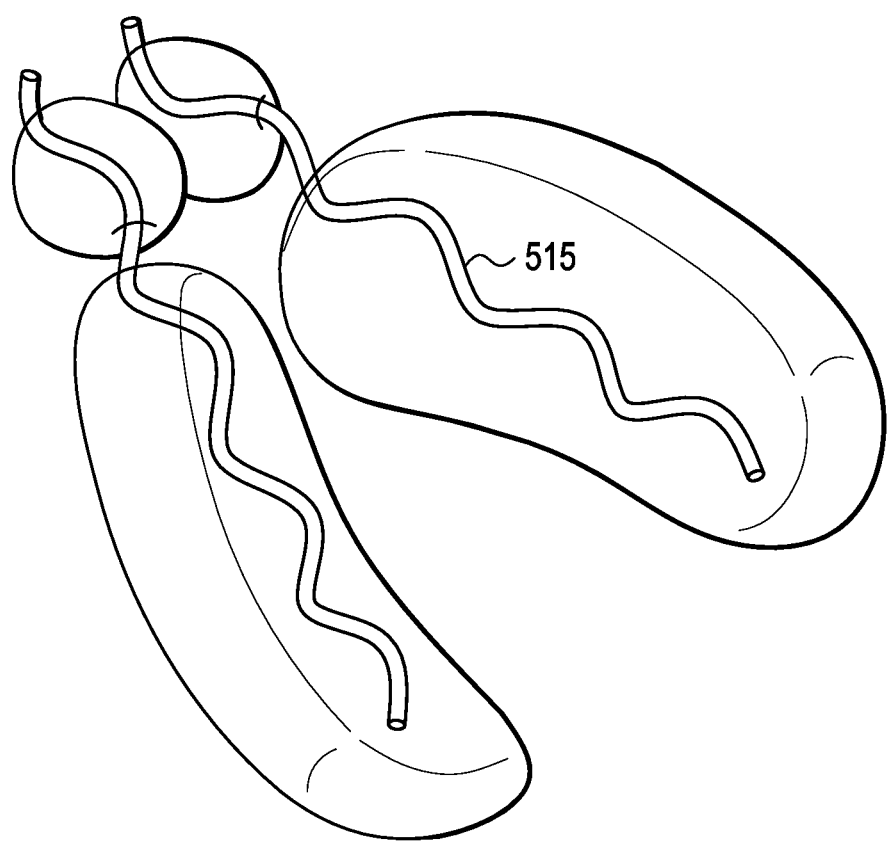
FIG. 18 discloses a perspective view of a helical fiber optic inserted diagonally downward into a substantia nigra from the third ventricle through the mammillary body.

It is further noted that, anatomically, the lateral portion of the mammillary body does not hang down into the interpeduncular fossa, but rather appears to be fully attached to the floor of the third ventricle. Because of this fusion of tissues, it appears that a relatively large diameter fiber optic can be safely passed through this region of the mammillary bodies without fear of disrupting fossa vascularity. Now referring to FIGS. 17a and 17b, in some embodiments associated with the traversal of the substantia nigra, the distal end portion 513 of fiber optic is completely helical. The helical nature of the fiber optic will allow the surgeon to substantially traverse the width of the substantia nigra with the fiber optic, thereby providing a substantially uniform illumination of the tissue within the helix. Therefore, when the distal end portion is helical, the helix provides a) uniform illumination of the substantia nigra which it encloses, and b) a sound anchor within the mammillary body and midbrain. FIG. 18 shows a helical fiber optic 515 embedded within both the mammillary body and substantia nigra, and traversing the substantia nigra with a downwards descent.

Figure 19:
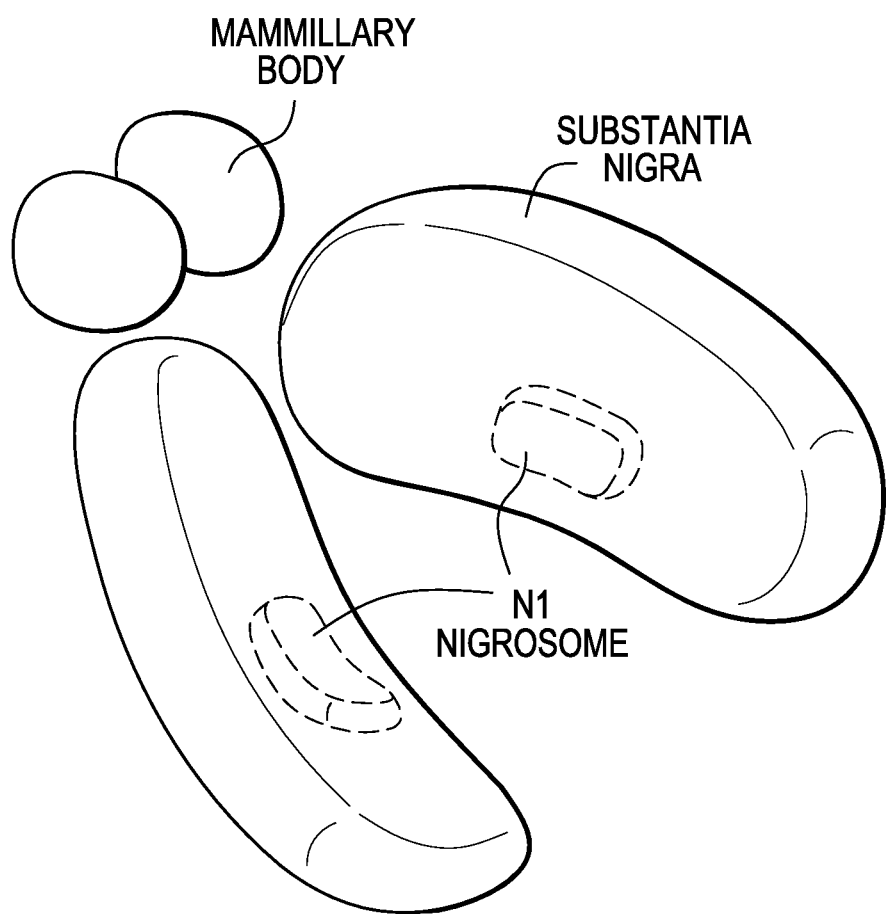
FIG. 19 discloses a perspective view of a substantia nigra containing an N1 nigrosome.

Damier, Brain 1999, August 122(Pt. 8; 1437-48 (Damier) reports on the heterogeneous nature of the substantia nigra pars compacta, and in particular on the clustering of dopaminergic neurons in regions five distinct regions labeled nigrosomes N1-N5. These nigrosomes, which comprise about 40% of the dopaminergic SN cells, are located in the intermediate-caudal regions of the substantia nigra. See FIG. 19. Damier further reports that these nigrosomes in general (and the N1 nigrosome in particular) appear to lead the SN in dopaminergic cell loss, both temporally and quantitatively.

It is believed by the present inventors that these nigrosomes should be specifically targeted for red/NIR light therapy. Therefore, in some embodiments of the present invention, the distal end of the fiber optic therapeutically irradiates at least one nigrosome of the SN. Preferably, the distal end of the fiber optic therapeutically irradiates at least the N1 nigrosome of the SN. More preferably, the distal end of the fiber optic therapeutically irradiates at least the N1 nigrosome of the SN with between 1 J/cm$^2$ and 10 J/cm$^2$ of red/NIR light. In some embodiments of the present invention, the distal end of the fiber optic is seated in the STN and therapeutically irradiates at least one nigrosome of the SN. In some embodiments of the present invention, the distal end of the fiber optic is seated in the PPN and therapeutically irradiates at least one nigrosome of the SN. In some embodiments of the present invention, the distal end of the fiber optic is seated in the SN and therapeutically irradiates at least one nigrosome of the SN. In some embodiments of the present invention, the distal end of the fiber optic is seated in the N1 nigrosome and therapeutically irradiates the N1 nigrosome of the SN.

Figure 20:
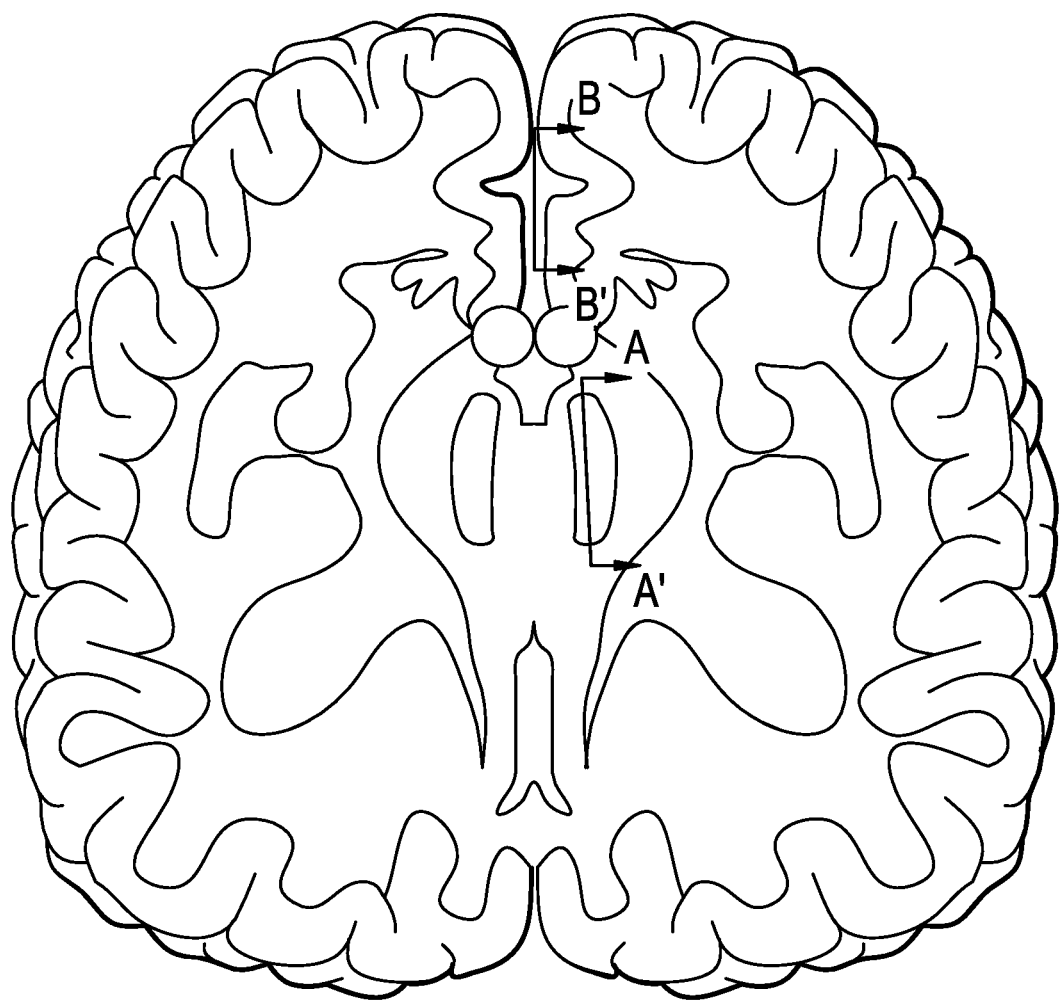
FIG. 20 discloses a horizontal cross section of an area surrounding a midbrain.
Figure 21A:
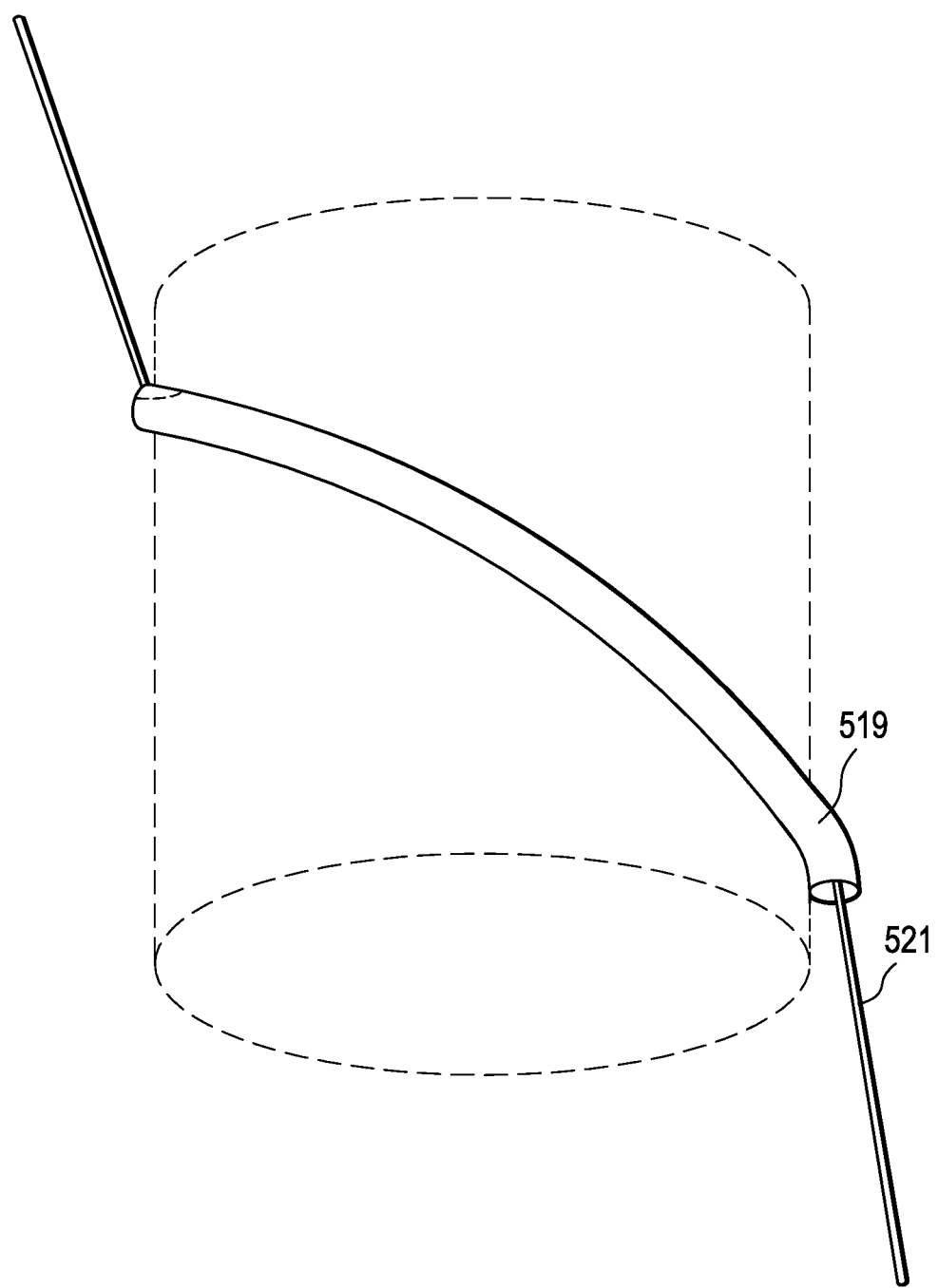
FIG. 21a discloses a semi-helical anchor tube extending for one-half a period.
Figure 21B:
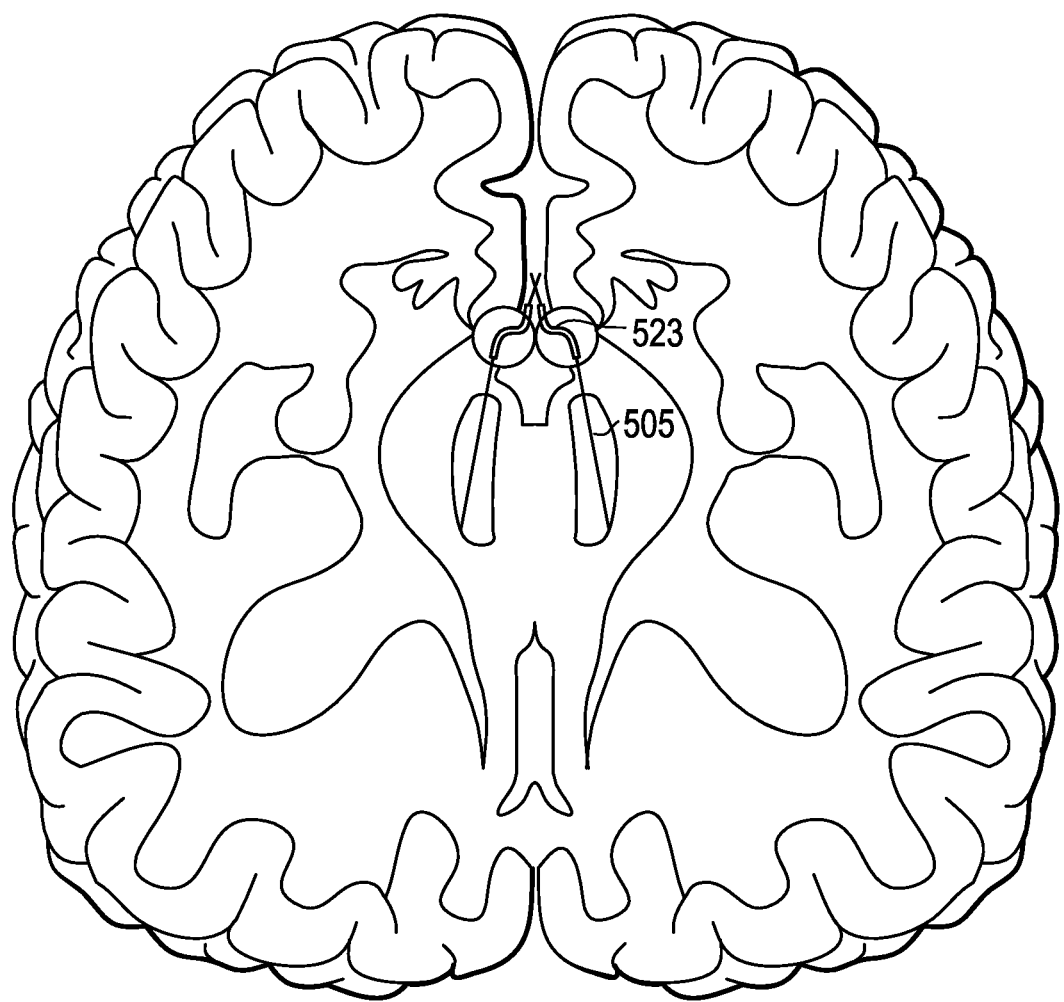
FIG. 21b discloses a semi-helical anchor tube inserted into a mammillary body, and a flexible fiber optic running through the anchor tube into the substantia nigra.

It is further noted that the axis of the substantia nigra (A-A' in FIG. 20) does not align with the axis of the 3$^{rd}$ ventricle (B-B' in FIG. 20), but rather runs substantially parallel to it. This "misalignment" of axes means that a straight fiber optic can not simply enter the mammillary body along the axis of the 3$^{rd}$ ventricle and continue on to traverse the substantial length of the substantia nigra. It is noted that a tube 519 in the form of one half period of a helix has the property of essentially laterally shifting the longitudinal axis of a fiber optic 521 running through it. See FIG. 21a. Therefore, in some embodiments, a hemi-helical anchor tube 523 is placed in the mammillary body in order to laterally shift the longitudinal axis of a fiber optic 525 running through it (see FIG. 21b). In some embodiments, the hemi-helical anchor tube is placed in the mammillary body by threading it into place with the help of a helical stylet.

Figure 22:
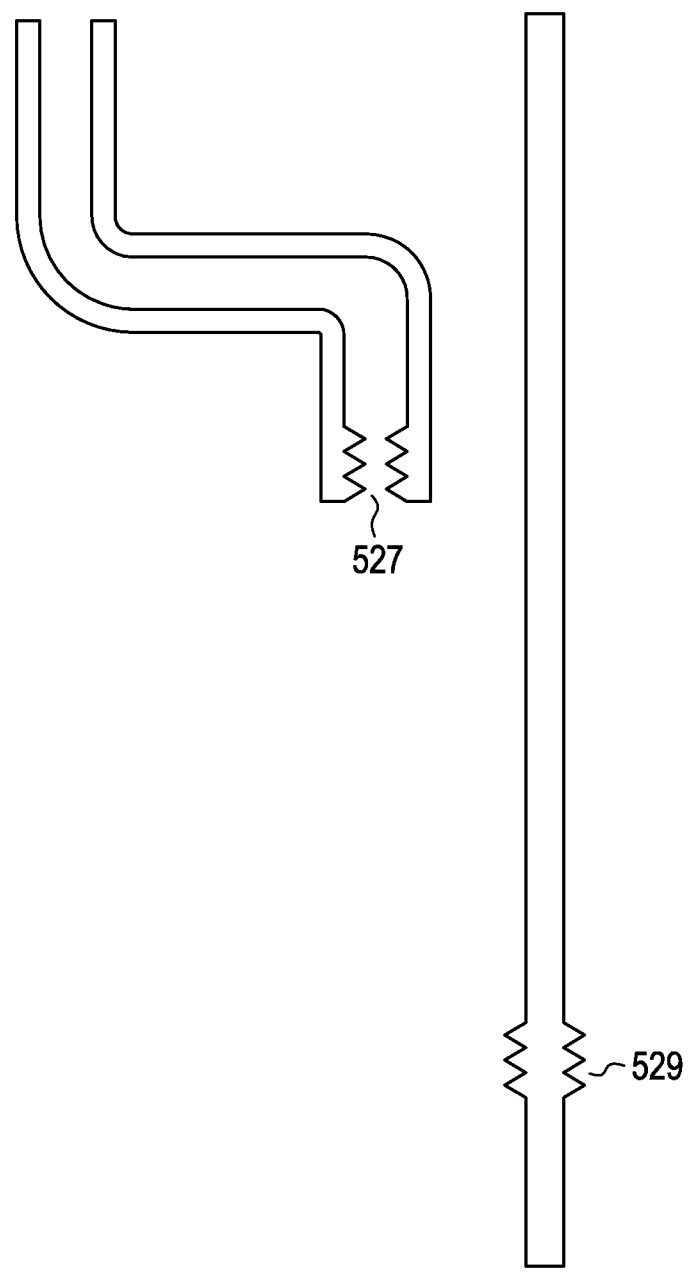
FIG. 22 discloses an anchor tube and a fiber optic, each having a mating threadform.

The use of a hemi-helical anchor tube of the present invention carries with it three advantages over a simple straight insertion of a straight fiber optic. First, as noted, laterally shift the longitudinal axis of a fiber optic running through it so that the fiber optic can traverse a greater portion of the substantia nigra. Second, it carries the fiber optic farther away from the interpeduncular fossa, thereby adding a measure of safety. Third, it provides a means of anchoring the fiber optic. The half-helical nature of the anchor tube provides a means of anchoring the tube in the mammillary body. See FIG. 22. The internal bore 527 of the hemi-helical anchor tube can be threaded to mate with a matching thread 529 upon the fiber optic. When the threaded potion of the fiber optic enters the tube, the fiber optic is rotated, thereby locking the fiber optic to the anchor tube.

Figure 23:
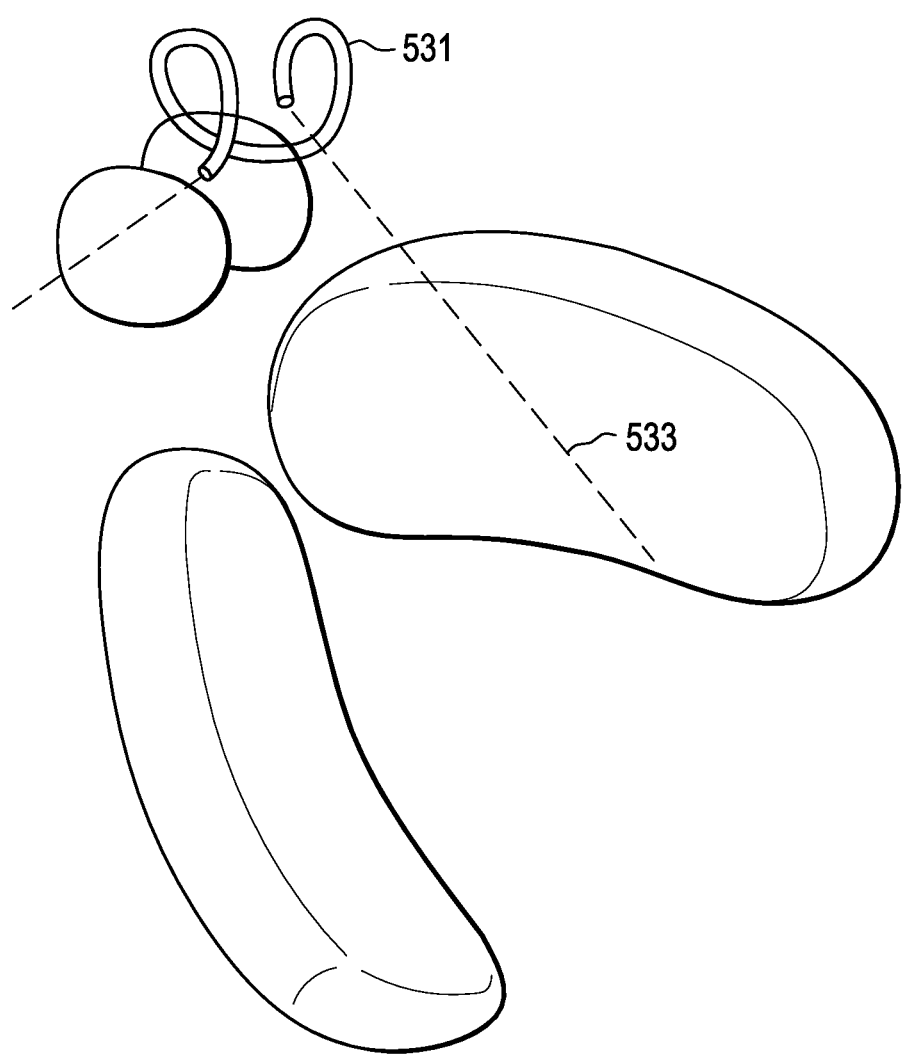
FIG. 23 discloses a helical anchor tube inserted into a mammillary body, with a fiber optic (in ghost) running through it and into the substantia nigra.

It is further noted that if the exit of the half-helical anchor tube is slightly varied to be slightly greater or less than one-half a period, then the plane upon which the fiber optic exits the tube can differ from the plane upon which the fiber optic exits the tube. Making such a tube 531 would allow the fiber optic 533 to enter the mammillary body in the horizontal plane of the midbrain and exit the mammillary body in a descending manner. Such a decent could be desirable because the substantia nigra extends significantly downward from the mammillary body (as shown in FIG. 23).

Figure 24A:
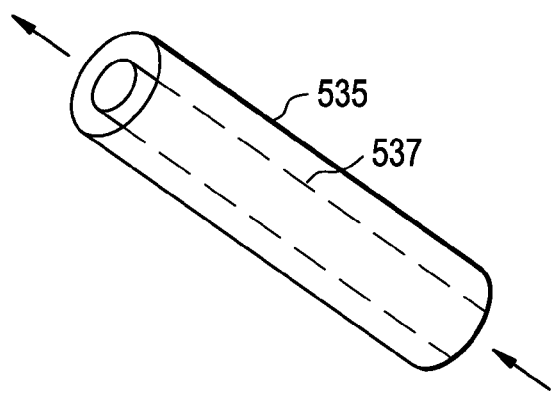
FIGS. 24a-c disclose three anchor tubes having different exit geometries.
Figure 24B:
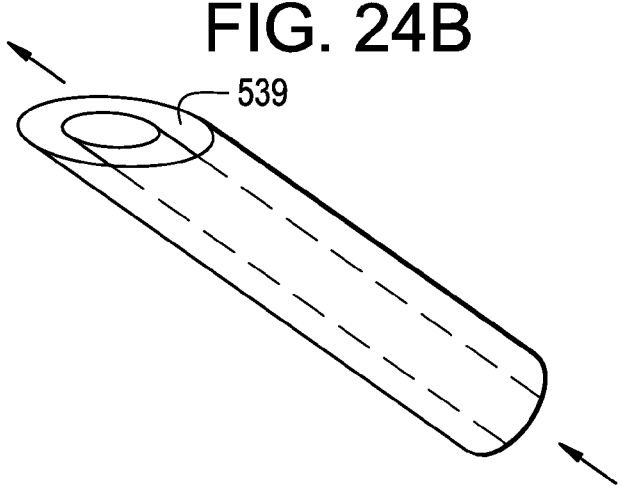
Figure 24C:
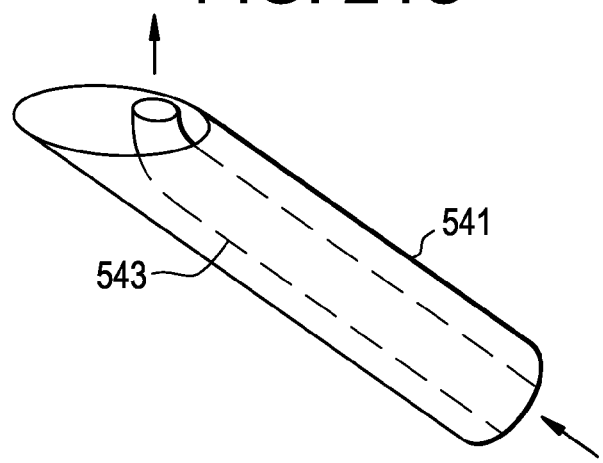

The direction of the fiber optic exiting the helix can be adjusted to the surgical need. In one embodiment, the outer surface of the helical tube remains helical, but the distal end of the inner bore is modified to alter the angle of exit. This property is demonstrated in FIGS. 24a-24c. FIG. 24a is a conventional helical tube portion 535 having a helical bore 537. The direction of the fiber optic exiting the tube (shown by the arrow) is equal to the tangent at the distal end of the tube. FIG. 24b is similar to FIG. 24a, but differs in that the exit surface 539 of the tube is angled. Again, the direction of the fiber optic exiting the tube (shown by the arrow) is equal to the tangent at the distal end of the tube. The helix of FIG. 24c has an outer surface 541 that has a helical shape, but its bore is modified in the area of the tube exit 543 to produce a different exit direction. Thus, modifying the bore at the exit will allow the production of a predetermined exit direction.

Figure 25A:
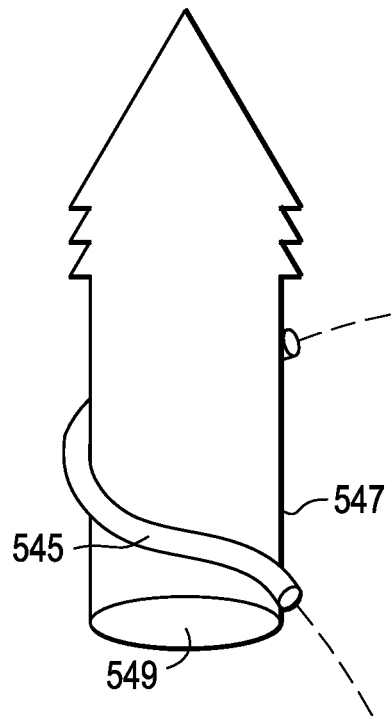
FIGS. 25a-d disclose various anchor tubes carried on the outer surfaces of cylindrical bodies.

In some embodiments, the hemi-helical anchor tube 545 is carried on the outer surface 547 of a cylindrical plug 549 (as shown in FIG. 25a). This embodiment simply requires the surgeon to linearly insert the plug into the mammillary body, taking care to orient the plug so that the entrance and exits of the tube are in their desired places.

Figure 25B:
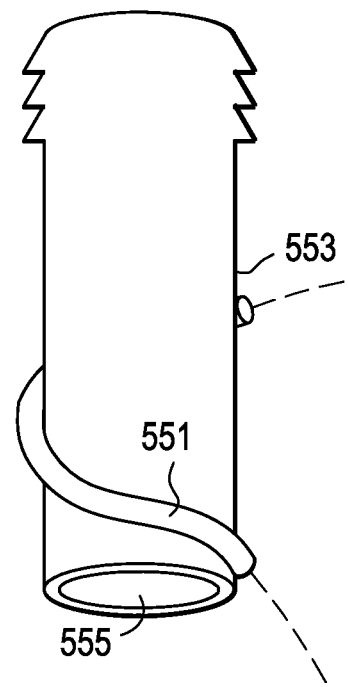

In some embodiments, the hemi-helical anchor tube 551 is carried on the outer surface 553 of a cylindrical annulus 555 (as shown in FIG. 25b). The annulus embodiment has all the advantages of the plug design discussed directly above, but causes less damage to the mammillary body.

Figure 25C:
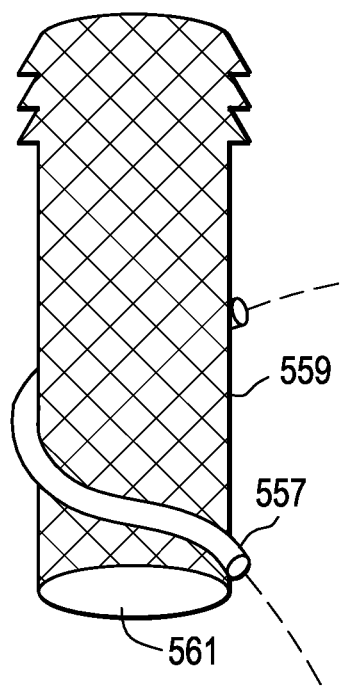

In some embodiments, the hemi-helical anchor tube 557 is carried on the outer surface 559 of a cylindrical mesh 561 (as shown in FIG. 25c). The mesh embodiment has all the advantages of the annular design discussed directly above, but allows for more repair of the mammillary body.

Figure 25D:
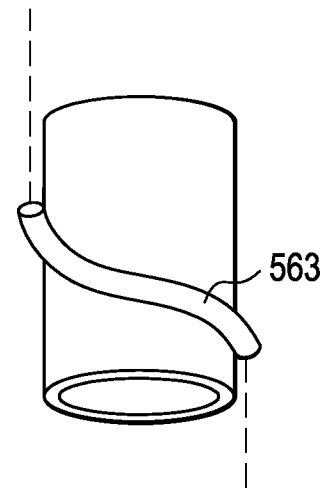

The anchor tube annulus combination of FIG. 25d is substantially similar to that of FIG. 25b, except that the anchor tube 563 runs for essentially one-half of a period. This device can be advantageously inserted into a mammillary body and thereby shift the axis of the fiber optic in a manner similar to that of FIG. 21b.

In some embodiments, the hemi-helical anchor tube is made of a shape memory metal that is inserted in a linear fashion and then bends into an angled shape upon heating.

Moreover, if the mammillary bodies are a redundant structure, then they can be over-irradiated without causing any overall harm.

If the therapeutic light treatment of the present invention can over-irradiate the mammilary bodies, then the surgeon is able to treat the mammillary body as an effective extension of the fiber optic. Thus, the treatment can irradiate the mammilary bodies so as cause the bodies to become an effective light source. This approach could decrease the distance of the "light source" to the substantia nigra from 1 cm (fiber optic-to-SN distance) to no more than about 0.5 cm (MB-to-SN distance), and even less in some areas wherein the mammillary body essentially abuts the substantia nigra. For example, this type of treatment may irradiate the mammillary bodies so that their posterior surfaces have a fluence of about 10 J/cm$^2$ of red/NIR light. Because there is nearly contact between the posterior portion of the MBs and the anterior tip of the substantia nigra (SN), the anterior tip of the SN will likely receive about 10 J/cm$^2$ of red/NIR light from the overirradiated MBs. Substantia nigral structure downstream of this tip will then receive the red/NIR light in a therapeutic dose of between 0.1 J/cm$^2$ and 10 J/cm$^2$. This could include an anterior span of the substantia nigra having a length of about 7 mm, or about half of the substantia nigra.

Likewise, if the center of the mammillary body is irradiated so that its posterior surface experiences a fluence of 100 J/cm$^2$, then (assuming a penetration depth of about 2 mm) the sphere of midbrain experiencing red/NIR light in the therapeutic range of about 20-0.01 J/cm$^2$ may have a radius of about 8 mm. Since the typical substantia nigra has a 5 mm height, a 15 mm length and a 3 mm width, this irradiation should beneficially irradiate substantially ⅔ of the substantia nigra. Moreover, if the red/NIR light is able to provide therapy at fluences as low as 0.001 J/cm$^2$ (as per Byrnes), then the radius of influence would be even larger.

Since the patient with Parkinson's Disease begins to display motor disabilities when about 80% of the dopaminergic substantia nigral neurons have died, it is believed that any treatment that therapeutically treats about 20% of the dopaminergic cells may have a significant impact. Therefore, a treatment involving overirradiation of the mammillary bodies that results in the ability to treat about half of the substantia nigra would appear to be worthwhile.

Therefore, the surgeon can place a fiber optic on the floor of the third ventricle (using ventriculostomy techniques) and irradiate just the mammillary bodies. This would effectively make the MBs a light bulb that shines therapeutic red/NIR light upon the substantia nigra.

Figure 26:
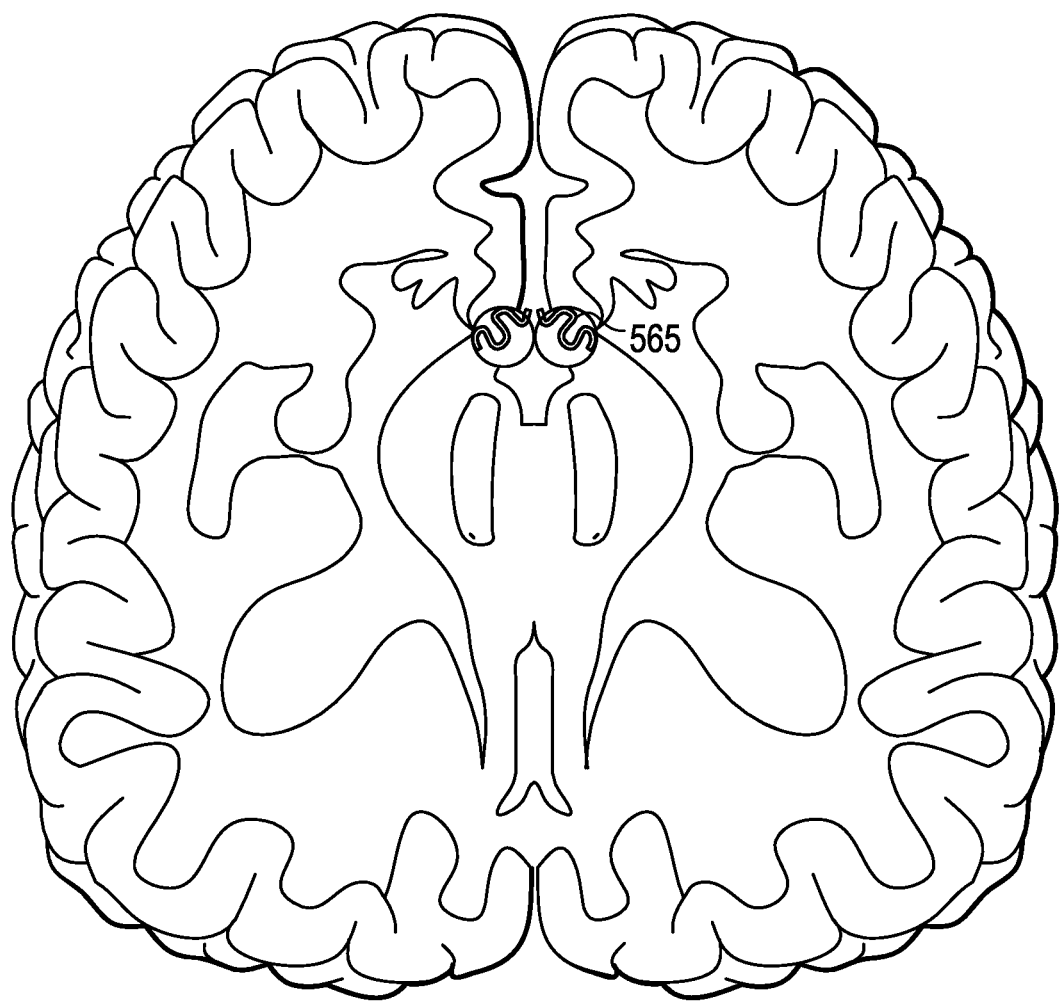
FIG. 26 discloses a helical fiber optic inserted into just the mammillary body from the third ventricle.

In some of these embodiments involving overirradiation of the mammillary bodies, and now referring to FIG. 26, a distal end 565 of a fiber optic is implanted into the mammillary body, and light is flowed into the mammillary body such that its posterior surface has a light fluence of about 10-100 J/cm$^2$. In some of these embodiments, the distal end of the fiber optic preferably has a helical shape. The helix structure performs three important functions. First, it anchors the fiber optic in the region of interest. Second, it provides uniform light within the internal structure of the mammillary bodies. Lastly, it may be sized so that its disappearance from the 3$^{rd}$ ventricular floor signals the surgeon that the helix has entered the mammillary body to a sufficient depth, thereby helping avoid its entering the interpeduncular fossa.

Figure 27:
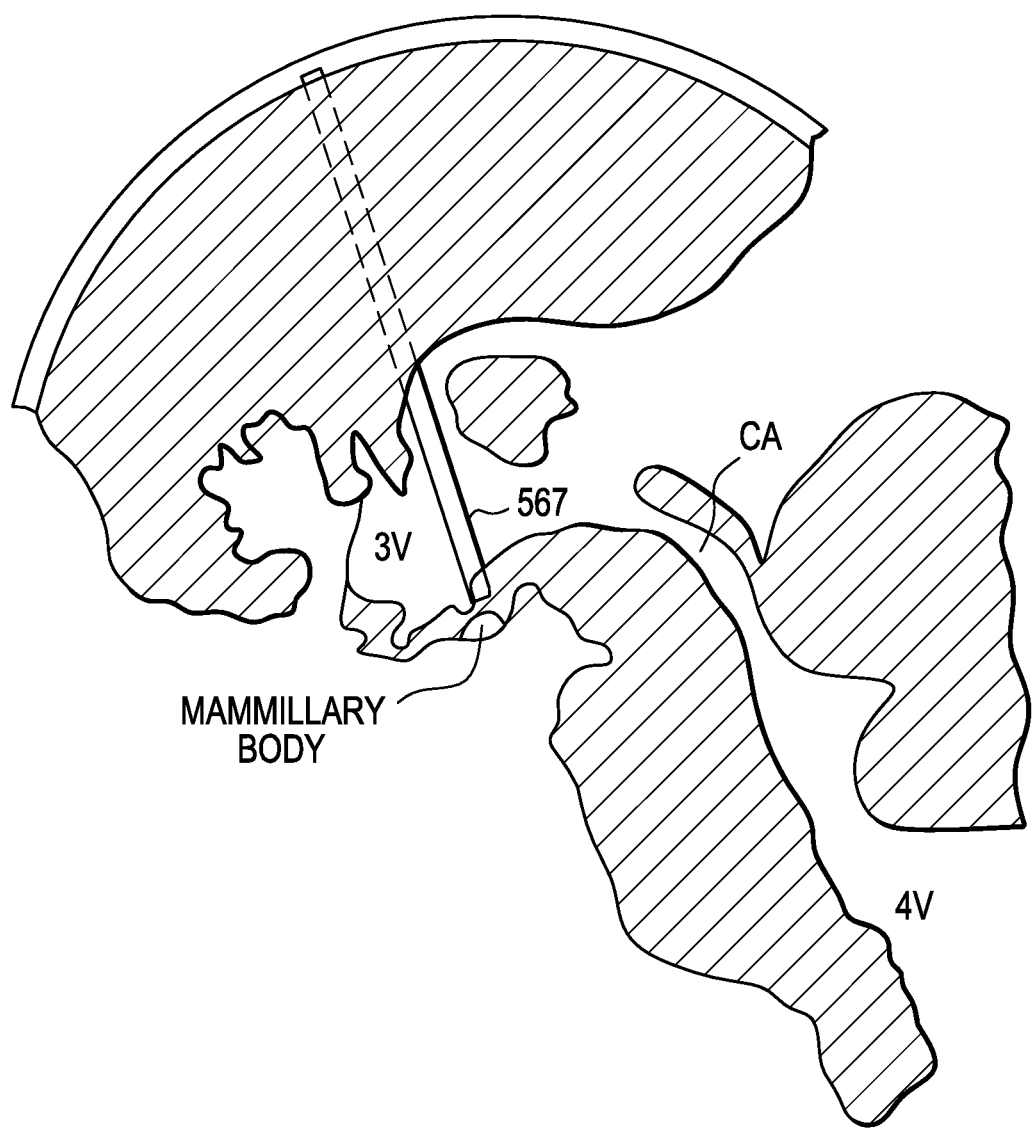
FIG. 27 discloses a saggital view of the human brain having an optical wave guide inserted into the third ventricle and bearing upon the floor of the third ventricle near the mammillary body.

In other embodiments, overirradiation of the mammillary bodies is accomplished without anchoring the fiber optic in the mammillary body. In these embodiments, and now referring to FIG. 27 anchoring the fiber optic 567 involves fixing a proximal portion of a rigid fiber optic to either the dura or skull. Such proximal anchoring, which is commonly adopted in the anchoring of electrodes for deep brain stimulation, would automatically fix the distal end of a semi-rigid, appropriately-sized fiber optic to the mammillary body. The fiber optic travels through a lateral ventricle, through the foramen on Monro, and seats upon the mammillary body.

Therefore, in some embodiments, a distal end portion of the fiber optic is placed on the floor of the anterior third ventricle while its proximal end is fixed to the skull or dura. If the floor of the third ventricle is a somewhat flexible structure so that it has an elastic response to pressure, then the length of the fiber optic could be set so that the distal end of the fiber optic is snuggly fit with the mammillary body. In this condition, slight distal movement of the fiber optic would provide a slightly more snug fit and slight proximal movement of the fiber optic would provide a slightly less but still snug fit. Throughout the range of movement, the distal end of the fiber optic could be in contact with the floor of the third ventricle next to the mammillary body.

This method of fixing a proximal portion of a rigid fiber optic to either the dura or skull has the advantage of avoiding any mechanical invasion of the mammillary body.

Therefore, in accordance with the present invention, there is provided a method of treating a patient having Parkinson's Disease, comprising the steps of:
a) providing an optical wave guide having a proximal end portion and a distal end portion;
b) endoscopically implanting the distal end portion of the optical wave guide onto a floor of the patient's third ventricle, and
c) delivering light through the optical wave guide to irradiate at least a portion of a substantia nigra with an effective amount of light.

Because the delivery and placement of the fiber optic takes places substantially entirely within the ventricular system of the brain, such delivery and placement may be performed endoscopically. The endoscopic delivery and placement of this system represents a significant advantage over the conventional stereotactically-guided placement of medical devices in the brain. First, whereas stereotactically guided systems require the use of expensive and complicated hardware, endoscopic placement of a tube within the cerebral aqueduct is relatively straightforward and can be performed without expensive and time-consuming support equipment. Second, stereotactically guided systems typically require blunt invasion of the brain parenchyma and its related vasculature, and so generate a risk of producing neural deficits and hemorrhage. For example, Kleiner-Fisman, *Mov. Disord.*, 2006, Jun. 21, Suppl. 14 S290-304 reports a 3.9% hemorrhage rate for Parkinson's patients receiving deep brain stimulation implants. In contrast, endoscopic placement of a fiber optic in the $3^{rd}$ ventricle does not produce any injury to the brain tissue or its related vasculature whatsoever, and so therefore should eliminate the risk of hemorrhage.

In sum, endoscopically accessing the ventricular system is much less complicated than placing a catheter directly into the brain parenchyma. Endoscopic access could be performed by most neurosurgeons and so there would be no need to require stereotactic-trained surgeons or stereotactic/navigation equipment. Most neurosurgeons are capable of and would be comfortable placing a tube into the lateral ventricle and driving that catheter into the floor of the third ventricle endoscopically and then into the mammillary body. Anatomic landmarks would facilitate its placement and this would obviate the need for complex stereotactic localizing techniques. It would a simpler procedure for patients and could be performed by most neurosurgeons.

Therefore, in accordance with the present invention, there is provided a method of treating a patient having Parkinson's Disease, comprising the steps of:
a) providing an optical wave guide having a proximal end portion and a distal end portion;
b) endoscopically implanting the distal end portion of the optical wave guide into the patient's mammillary body, and
c) delivering light through the optical wave guide to irradiate at least a portion of a substantia nigra with an effective amount of light.

In some embodiments using endoscopic placement, a modified procedure of Farin, "Endoscopic Third Ventriculostomy" *J. Clin. Neurosci.* August; 13(7):2006, 763-70 is used. In particular, a burr hole is made through the skull at the intersection of the coronal suture and the midpupillary line, approximately 2-3 cm lateral to the midline. The endoscope trajectory is aimed medially toward the medial canthus of the ipsilateral eye and toward the contralateral external auditory meatus in the anterior/posterior plane. This approach leads to the foramen of Monro and floor of the third ventricle. The lateral aspect of the anterior (adult) fontanelle is targeted. The dura is opened. The lateral ventricle is tapped using a peel-away sheath with ventricular introducer. The sheath is secured in place to the scalp. A rigid neuroendoscope is then inserted into the lateral ventricle, and the choroid plexus and septal and thalamostriate veins are identified in order to locate the foramen of Monro. The endoscope is advanced into the third ventricle. The mamillary bodies are some of the more posterior landmarks of the third ventricle; moving anteriorly, the basilar artery, dorsum sellae and infundibular recess may be obvious based on the degree of attenuation of the ventricular floor. The endoscope is then moved farther posteriorly to the mammillary bodies. The endoscope then deposits the distal end of the fiber optic in the mammillary body.

This endoscopic approach provides both a safety, time and efficacy advantage over stereotactic placement of fiber optics in various midbrain structures.

First, since there is about a 4% risk of hemorrhage associated with STN deep brain stimulation, it is reasonable to expect that stereotactic placement of the fiber optic near the substantia nigra will have a similar risk (or twice that 4% risk for bilateral fiber optic placement). In contrast, the endoscopic placement of fiber optics through the third ventricle will likely eliminate that risk.

Second, stereotactic placement of bilateral fiber optics near the substantia nigra requires bilateral access and so requires making two burr holes in the cranium. In contrast, endoscopic placement of fiber optics through the third ventricle requires only a single access hole in the cranium. In some embodiments, bilateral placement of fiber optics in the mammillary bodies is accomplished endoscopically through the same opening in the cranium. Because the mammillary bodies are adjacent to each other on the floor of the third ventricle, only a single approach need be made. In preferred embodiments, a single opening in the skull is made and a path is bored through the brain to the anterior portion of the lateral ventrical. Each of the optical fibers is then fed down this path and enters the same lateral ventricle from the cranium. Next, the fibers are guided through the pertinent foramen of Monro, pass downward through the third ventricle to its floor, and are placed into or on one of the adjacent mammillary bodies.

Third, whereas anchorage of the stereotactically placed fiber optics will likely adopt the DBS method of anchoring a proximal portion of the fiber optic to the skull or dura, many of the embodiments disclosed above use anchorage of helices in the mammillary bodies and so is a much simpler anchorage procedure.

Fourth, stereotactic placement of bilateral fiber optics near the substantia nigra uses an approach that is essentially transverse to the length of the substantia nigra, and so irradiates only a small portion of the substantia nigra. In contrast, endoscopic placement of fiber optics through the third ventricle and mammillary bodies uses an approach that is well suited to allowing the surgeon to traverse the entire length of the substantia nigra with the fiber optics.

In other endoscopic embodiments, the optical wave guide and/or light source is placed in the anterior horn of the lateral ventricle, and light emanating therefrom therapeutically irradiates the caudate nucleus.

Therefore, in accordance with the present invention, there is provided a method of treating a patient having Parkinson's Disease, comprising the steps of:
  a) providing an optical wave guide having a proximal end portion and a distal end portion;
  b) endoscopically implanting the distal end portion of the optical wave guide into an anterior horn of the patient's lateral ventricle, and
  c) delivering light through the optical wave guide to irradiate at least a portion of a caudate nucleus with an effective amount of light.

Therefore, in accordance with the present invention, there is provided a method of treating a patient having Parkinson's Disease, comprising the steps of:
  a) providing an red/NIR LED,
  b) endoscopically implanting the LED into an anterior horn of the patient's lateral ventricle, and
  c) delivering light from the LED to irradiate at least a portion of a caudate nucleus with an effective amount of light.

In some embodiments, a unilateral fiber optic is passed through a lateral aspect of a single mammillary body. Blair, *J. Neuroscience*, Aug. 1, 1999, 19(15) 6673-83 examined the effect of lesioning one and both of the mammillary bodies in rats, and reports that anterior thalamic head-direction signal is abolished by bilateral but not unilateral lesions of the lateral mammillary nucleus. Blair concludes that the lack of damage in the unilateral model is due to the fact that a single lateral mammillary nucleus projects bilaterally to each anterodorsal thalamus. Therefore, it appears that there is substantial redundancy in the circuitry of a pair of lateral mammillary nuclei.

Figure 28:
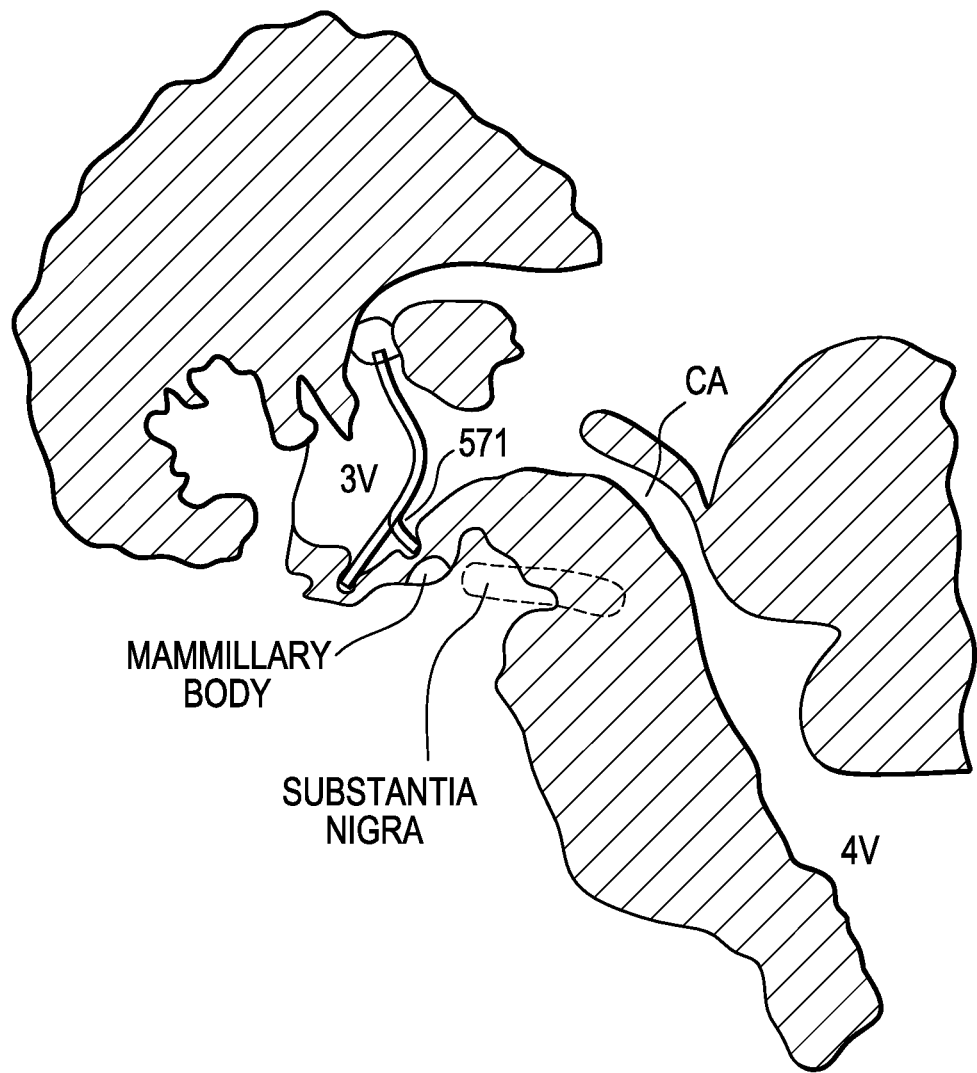
FIG. 28 discloses a saggital view of the human brain having a tripod instrument inserted onto the floor of the third ventricle.

In embodiments in which the fiber optics pierce the mammillary bodies, it is important to attain the proper angle of entry. This angle should be sufficiently wide in the horizontal plane in order to avoid entering the interpeduncular fossa. This angle should also be sufficiently axial in the sagittal plane in order to angle downward into the middle of the substantia nigra. These angles can be determined from preoperative MRIs. Now referring to FIG. 28, once the appropriate angle has been established, the distal end of the endoscope can be made into a tripod 571 that mimics the appropriate angle of entry when placed in the middle of the mammillary bodies.

In some embodiments, the fiber optic is run through the temporal horn of the lateral ventricle, exiting the lateral ventricle at the choroidal fissure. The choroidal fissure is a gap located on the medial wall of the anterior end of the temporal horn of the lateral ventricle. The choroidal fissure essentially opens onto a posterior portion of the substantia nigra (located next to the medial geniculate nucleus).

Figure 29:
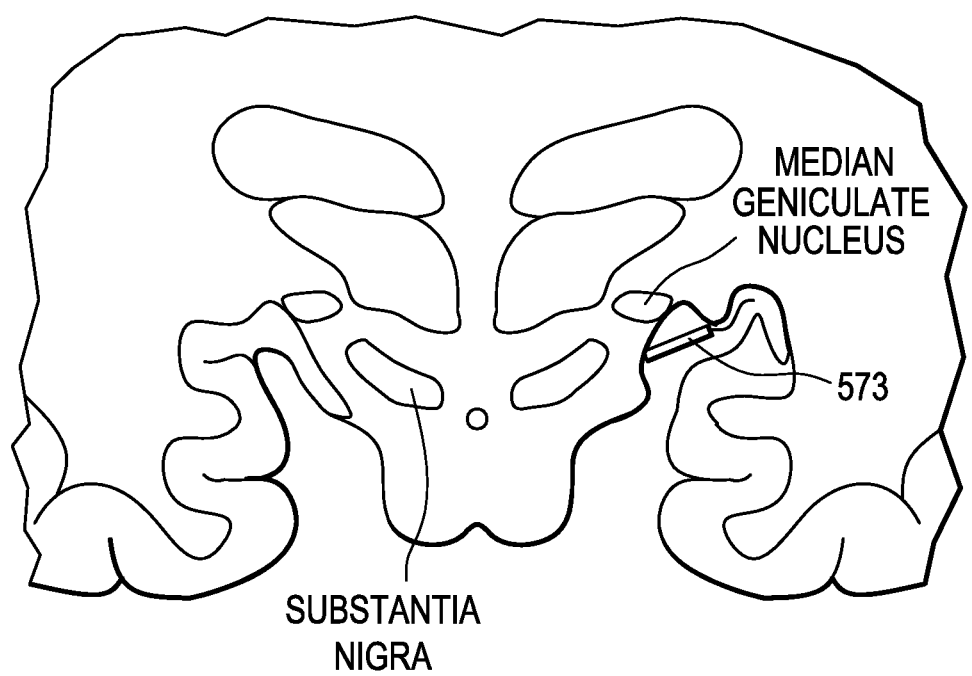
FIG. 29 discloses a cross-section of the midbrain showing the medial geniculate nucleus adjacent the dorsal portion of the substantia nigra.

Thus, in these embodiments using the choroidal fissure as a pathway, and now referring to FIG. 29, the distal end 573 of the fiber optic may be advantageously placed on the outer surface of the midbrain adjacent to the posterior portion of the substantia nigra. From this position, the fiber optic may non-invasively illuminate the posterior portion of the substantia nigra.

It is believed that illuminating the posterior portion of the substantia nigra will produce a therapeutic benefit. It is believed that patients with Parkinson's Disease begin to experience motor symptoms when less than about 20% of their substantia nigra cells survive. It is further believed that illuminating the outer surface of the midbrain from a location next to the medial geniculate nucleus will beneficially irradiate at least about 25% of the substantia nigra. Accordingly, this therapy should serve to save and/or regrow enough of the substantia nigra to reduce and/or eliminate PD disabilities.

In some embodiments, the distal end portion of the fiber optic comprises a tubular shape that is anchored within the choroidal fissure. If required, the choroidal fissure may be fenestrated or opened in order to accommodate the distal end portion of the fiber optic.

In some embodiments involving access to the substantial nigra through the choroidal fissure, bilateral placement of fiber optics in the lateral ventricles is accomplished through the same opening in the cranium. Whereas the first fiber optic remains in the lateral ventricle that it initially enters, the second fiber optic is guided through the first foramen of Monro, through the third ventricle, through the second foramen of Monro and into the second lateral ventricle. In this way, only a single opening in the skull need be made in order to have bilateral treatment of the substantia nigra structures.

Some embodiments of the present invention involve access to the substantia nigra through the ambient cistern. For example, these approach could include an approach through the choroidal fissure, or through a supracerebellar or subtemporal approach. In these embodiments, the distal end of the fiber optic is advanced through the ambient cistern to the tip of the substantia nigra adjacent the medial geniculate nucleus, and is then inserted into the substantia nigra, and is advanced to the opposite corner of the substantia nigra structure. In this manner, illumination of the distal end portion of the fiber optic will result in an illumination of the substantial breadth of the entire substantia nigral structure, from the lower posterior corner to the upper anterior corner.

Therefore, in accordance with the present invention, there is provided an implant for treating Parkinson's disease comprising:
  a) an implantable energy storage device (such as a battery),
  b) a Red/NIR light emitting diode (LED) in electrical connection with the implantable energy storage device, and
  c) an optical wave guide having a helical portion.

Therefore, in accordance with the present invention, there is provided a method of treating a patient having a neurodegenerative disease (such as Parkinson's disease), comprising the steps of:
a) providing an implant comprising:
   i) an implantable electrical power source (such as a battery),
   ii) a Red/NIR light emitting diode (LED) in electrical connection with the implantable energy storage device, and
   iii) an optical wave guide having a helical portion, the guide extending from the LED,
b) extracranially implanting the power source in the patient (preferably, in the chest of the patient),
c) implanting the LED within the skull of the patient (preferably within a ventricle), and d) implanting the optical wave guide within the brain of the patient (preferably, near the substantia nigra), and
e) activating the power source to cause red/NIR light irradiation of the brain of the patient.

We claim:

1. A method of treating a patient having a neurodegenerative disease, comprising the steps of:
   a) selecting an optical wave guide having a proximal end portion and a distal end portion;
   b) endoscopically implanting the distal end portion of the optical wave guide into a lateral ventricle of the patient, and
   c) delivering light through the optical wave guide to irradiate at least a portion of a subventricular zone with an effective amount of light.

2. A method of treating stroke, comprising the steps of:
   a) selecting a stroke patient, and
   b) delivering a distal end portion of an optical wave guide into a lateral ventricle of the patient, and
   c) irradiating through the optical wave guide at least a portion of a subventricular zone of the patient with an effective amount of red/NIR light.

* * * * *